(12) United States Patent
Shanks et al.

(10) Patent No.: US 8,058,000 B2
(45) Date of Patent: *Nov. 15, 2011

(54) SPECIES-SPECIFIC PRIMER SETS AND IDENTIFICATION OF SPECIES-SPECIFIC DNA SEQUENCES USING GENOME FRAGMENT ENRICHMENT

(75) Inventors: Orin C. Shanks, Cincinnati, OH (US); Jorge Santo Domingo, Cincinnati, OH (US); James E. Graham, Louisville, KY (US); Jingrang Lu, Mason, OH (US)

(73) Assignee: The United States of America as represented by the U.S. Environmental Protection Agency, Washington, DC (US)

( * ) Notice: Subject to any disclaimer, the term of this patent is extended or adjusted under 35 U.S.C. 154(b) by 68 days.

This patent is subject to a terminal disclaimer.

(21) Appl. No.: 12/429,545

(22) Filed: Apr. 24, 2009

(65) Prior Publication Data
US 2009/0203032 A1 Aug. 13, 2009

Related U.S. Application Data

(63) Continuation-in-part of application No. 11/316,888, filed on Dec. 27, 2005, now Pat. No. 7,572,584.

(60) Provisional application No. 60/686,407, filed on Jun. 2, 2005.

(51) Int. Cl.
*C12Q 1/68* (2006.01)
*C07H 21/00* (2006.01)
*C07H 21/02* (2006.01)
*C07H 21/04* (2006.01)

(52) U.S. Cl. .......... 435/6; 536/22.1; 536/23.1; 536/24.3

(58) Field of Classification Search ..... 435/6; 536/23.1, 536/24.3, 22.1
See application file for complete search history.

(56) References Cited

U.S. PATENT DOCUMENTS

| | | | |
|---|---|---|---|
| 5,436,142 A | 7/1995 | Wigler et al. | |
| 6,197,501 B1 * | 3/2001 | Cremer et al. | 435/6.14 |
| 6,287,825 B1 | 9/2001 | Weissman et al. | |
| 6,316,192 B1 | 11/2001 | Luo | |
| 6,344,316 B1 * | 2/2002 | Lockhart et al. | 506/9 |
| 6,936,442 B2 | 8/2005 | Pichuantes et al. | |
| 2003/0228599 A1 | 12/2003 | Straus | |
| 2005/0181355 A1 | 8/2005 | Greener et al. | |

OTHER PUBLICATIONS

Elsas et al., J. of Microbiological Methods. 43 : 197 (2001).*
Bernhard, et al., "A PCR Assay to Discriminate Human and Ruminant Feces on the Basis of Host Differences in *Bacteroides-prevotella* Genes Encoding 16S R RNA", Applied and Environmental Microbiology, 2001, pp. 457-457A, vol. 66, No. 10.
Diatchenko, et al., "Suppressive Subtractive Hybridization: A Method for Generating Differently Regulated or Tissue-Specific CDNA Probes and Libraries", PNAS, 1996, pp. 6025-6030, vol. 93.
Galbraith, et al., "Suppressive Substractive Hybridization as a Tool for Identifying Genetic Diversity in an Environmental Metagenome: The Rumen as a Model", Environmental Microbiology, 2004, pp. 928-937 vol. 6 No. 9.
Kandpal et al., "Chromosome Fishing: An Affinity Capture Method for Selective Enrichments of Large Genomic Fragments", Methods in Enzymology, 1992, pp. 39-54, vol. 216.
Lisitsyn, et al., "Cloning the Differtence Between Two Complex Genomes," Science, 1993, pp. 948-951, vol. 259.
Makrigiorgos, et al.,"A PCR- Based Amplification Method Retaining the Quantitative Difference Between Two Complex Genomes", Nature Biotechnology, 2002, pp. 936-939, vol. 20.
Nguyen, et al.,"Suppresive Subtractive Hybridization of and Differences in Gene Expression Content of Calcifying and Noncalcifying Cultures of *Emiliania huxleyi* Strain 1516", Applied and Environmental Microbiology, 2005, pp. 2564-2575, vol. 71, No. 5.
Straus, et al.,"Genomic Subtraction for Cloning DNA Corresponding to Deletion Mutations", PNAS, 1990, pp. 1889-1893, vol. 87.
Tinsley, et al.,"Analysis of the Genetic Differences Between *Neisseria meningitidis* and *Neisseria gonorrhoeae*: Two Closely Related Bacteria Expressing Two Different Pathogenicities," PNAS,1996, pp. 11109-11114, vol. 93.

* cited by examiner

*Primary Examiner* — Ethan C Whisenant
(74) *Attorney, Agent, or Firm* — Anne Kornbau; Browdy & Neimark, PLLC

(57) ABSTRACT

Targeted sequencing of genetic regions that differ between two DNA preparations uses genomic fragment enrichment. This method can be used to study genetic variation among closely related species and microbial communities, particularly for identifying sources of fecal pollution.

10 Claims, 7 Drawing Sheets

FIGURE 4A-C.

FIGURE 7
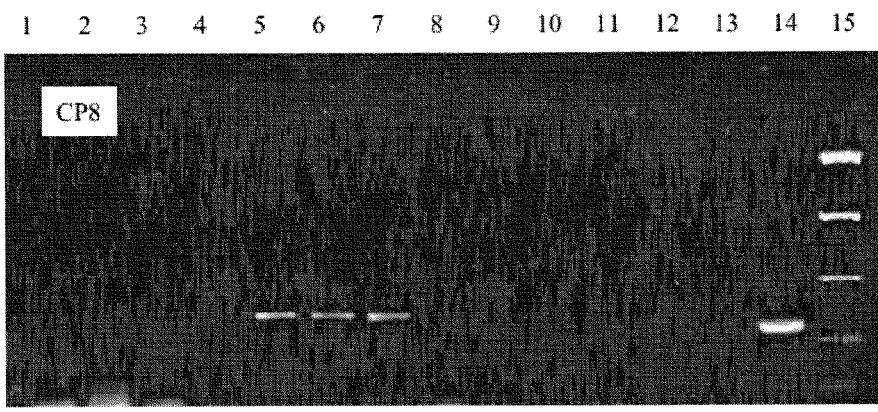
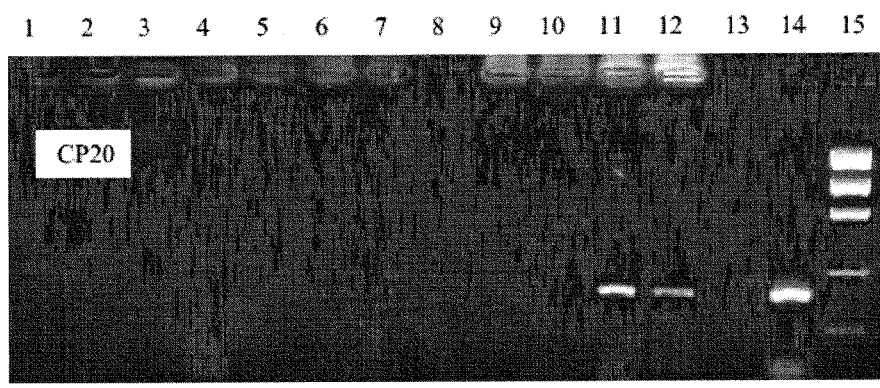
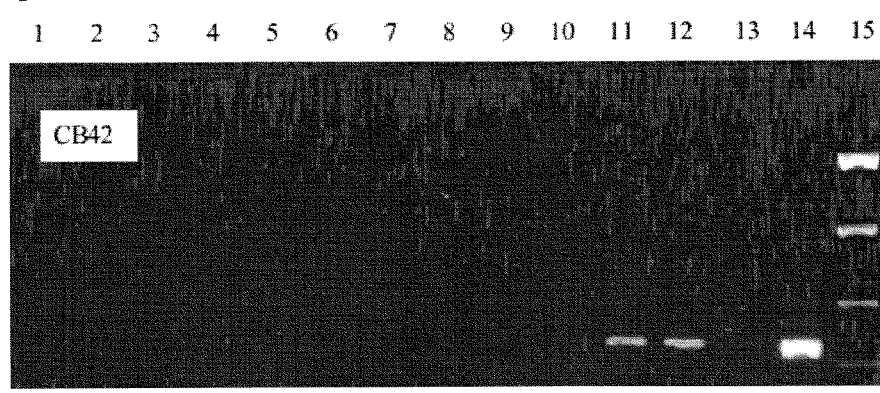

SPECIES-SPECIFIC PRIMER SETS AND IDENTIFICATION OF SPECIES-SPECIFIC DNA SEQUENCES USING GENOME FRAGMENT ENRICHMENT

CROSS-REFERENCE TO RELATED APPLICATIONS

The present application is a continuation in part of application Ser. No. 11/316,888, filed Dec. 27, 2005, which claims priority from provisional application Ser. No. 60/686,407, filed Jun. 2, 2005, the entire contents of all of which are hereby incorporated by reference.

FIELD OF THE INVENTION

The present invention relates to methods for using a specific method of solution phase competitive DNA hybridization, referred to as "Genome Fragment Enrichment" to identify microbial DNA sequences for determination of different sources of fecal contamination. The invention also relates to using this method for comparing bacterial genomes, and developing specific PCR primer sets to differentiate among bacterial species, strains, and sources of pollution.

BACKGROUND OF THE INVENTION

Poultry farming for meat production has significantly increased in the last few decades. For example, the per capita consumption of chicken in the United states was estimated to be over 74 pounds in 2004, which represents a 200% increase in less than 20 years, according to the U.S. Department of Agriculture. As a result of this increase in production, fecal matter has become a significant byproduct of the poultry industry. Fecal matter is often used as fertilizer in the form of raw or composted manure. A potential risk arising from the disposal of poultry waste is the spread of enteric pathogens, such as *Escherichia coli* O157:H7, *Salmonella* spp., and *Campylobacter* spp. These pathogens can reach watersheds after rainfall, and thereby increase risks associated with recreational use of waterways. Furthermore, environmental concerns also include high nutrient loads, such as nitrate and phosphate, from runoff to streams, ponds, and ground water. Methods that can specifically detect poultry fecal pollution are therefore needed to assist in the development and evaluation of adequate management practices targeting pollution control.

Current regulatory methods used to assess microbial water quality rely on measuring the levels of culturable fecal indicator bacteria such as Enterococci and other fecal coliforms. However, the plate culture approach cannot discriminate among different among specific bacterial strains or animal sources of fecal contamination.

A limited number of studies have reported on the use of genotypic methods to identify the presence of poultry fecal contamination in surface waters. Ribotyping and rep-PCR DNA fingerprint techniques targeting *E. coli* isolates have been applied to discriminate among different animal fecal sources, including chicken and human fecal sources. However, the successful application of these genotypic methods depends on the development of large fingerprint databases of indicator bacterial isolates, primarily *E. coli*. Moreover, the use of *E. coli* for fecal source identification has been recently criticized in light of the abundance of secondary habitat populations that are capable of adapting to conditions outside of the animal gut and, as a result, contribute to the levels of fecal indicator bacteria in water.

Recently, Field and coworkers used library-independent methods based on ribosomal 16S rRNA gene (i.e., 16S sDNA) sequences of *Bacteroides*-like bacteria to discriminate between human and ruminant feces. These *Bacteroides* markers have been used to identify non-point sources of fecal pollution in coastal in inland waters. Analyses of bacterial rDNA sequences from chicken fecal DNA extracts suggests that chicken cecum and ileum are inhabited by a diverse bacterial community. Although the chicken fecal communities are different from cattle and human fecal microbial communities, thus far no studies have demonstrated the value of 16S rDNA sequences to design host-specific genetic markers. Moreover, to date, there are no non-16S rDNA library-independent assays that can determine the presence of chicken fecal pollution in watersheds.

Functional genes involved in host-microbial interactions may represent a good pool of targets for host-specific assays. Some of these functional genes are hypothesized to be microbial surface proteins, while others may be associated with cellular processes and metabolism. However, a limited number of studies have used genes involved in host-microbial interactions as potential fecal community markers. This is probably due to the small number of microbial genes known to be involved in host-microbial interactions and the limited sequence information for these genes.

There is a demand for accurate microbial source tracking (MST), because of language in the U.S. Clean Water Act regarding total maximum daily loads (TMDLs) and protection of supplies of drinking water. Current PCR-based MST approaches focus on various specific known DNA sequences, mostly targeting 16S rRNA (rDNA) genes, once thought to be source specific. However, validation studies are constantly uncovering exceptions and limitations with existing MST technologies. A significant part of the problem with existing 16S rDNA-based MST methods stemmed from the inability to target microorganism DNA sequences encoding for proteins directly involved in host-microbe interactions, which are expected to contain high levels of genetic variation related to survival within different animal hosts.

Many specific approaches have previously attempted to determine sources of fecal contamination in the environment. One of the most widely used techniques is a PCR-based method that identifies ruminant fecal pollution by targeting bacterial 16S rDNA sequences from *Bacteroides* (Bernard and Field, AEM 66:4571-4574, 2000). The present inventors have conducted ongoing validation studies of this method, and have discovered that previously described proposed ruminant specific markers can amplify rDNA from non-ruminant fecal samples collected from geographic regions outside the original watersheds sampled. By definition, these previously described PCR target regions identify cow, deer, elk, goat, sheep, and other ruminants and pseudo-ruminants. This approach is therefore less useful in watersheds impacted by more than one ruminant animal source.

While advances in DNA sequencing and computational biology allow scientists to compare entire microbial genomes and discern microorganism-specific genetic information, sequencing of multiple closely related bacterial genomes so far remains prohibitively expensive and impractical for all but a very small number of laboratories. The entire genome content of more than 238 bacterial species have so far been defined through whole genome sequencing of representative type strains, and the number of genome sequences continues to increase. While significant differences in the genome content of different species are well-established, comparisons between genomes of closely related bacteria are equally important. These comparisons can provide species and strain-specific genetic information, define metabolic pathways and virulence factors, and provide insights into capacities for host-interactions, cell-to-cell signaling, stress response, and other essential microbial cellular functions.

Current DNA-based technologies potentially capable of identifying source, species, and strain-specific genetic markers include Suppressive Subtractive Hybridization (SSH) (Diatchenko et al., *PNAS* 93:6025-6030, 1996). This technique uses intentionally biased PCR amplification of nucleic acid pools to enrich for unique segments of restricted DNA relative to non-target DNA. SSH has been successfully applied in several pair-wise comparative genome studies (e.g., Nguyen et al., 2004, *AEM* 71 2564-2575), but only on one "metagenomic" or total microbial community DNA study (Galbraith et al., 2004; *Environmental Microbiology:* 928-937). SSH is a negative selection process that relies on unequal PCR amplification to amplify all dissimilar sequences from two nucleic acid pools. This is achieved by adding different self-complementary flanking regions to each of two fragment pools, and inhibition of amplification of only those duplexes that re-anneal relative to new heteroduplexes that form following denaturation and reassociation of the mixture.

One of the limitations of currently available microbial source tracking (MST) methods arises from the inability of previously described techniques to target microorganism DNA sequences potentially encoding proteins directly involved in host-microbe interactions. These regions, unlike rDNA operons, are expected to retain high levels of genetic variation in microbes found in association with different animal hosts.

SUMMARY OF THE INVENTION

It is an object of the present invention to use the Genome Fragment Enrichment (GFE) method to identify species, strain and host-specific microbial DNA sequences.

It is a further object of the present invention to provide methods for identifying whether microbial DNA from a specific animal source is present in fecal-contaminated material.

It is still another object of the present invention to identify the described DNA sequences from *Bacteroidales*-like microorganisms.

It is another object of the present invention to develop PCR primer deoxyoligonucleotide pairs to differentiate among microorganisms and host animals with respect to origins of pollution.

Genome Fragment Enrichment (GFE) method is used to select for genomic regions that differ among different fecal metagenomes.

A competitive hybridization method is used to enrich for DNA metagenomic fragments specific to chicken fecal DNA. Most metagenomic clones were predicted to be similar to bacterial normally present in the chicken fecal microbial community. The cloned fragments were used to develop chicken-specific assays that were challenged using chicken and non-chicken DNA fecal extracts. The assays suggest that some genetic markers are conserved in bacteria present in the avian gastrointestinal tract.

Competitive DNA hybridizations were performed between chicken fecal DNA and pig fecal DNA (CP) and between chicken fecal DNA and an avian DNA composite consisting of turkey, goose and seagull fecal DNA extracts (CB) to search for chicken-specific DNA fragments.

The present invention provides a positive DNA selection approach designated Genome Fragment Enrichment (GFE) technique, and its efficient use in identifying both unique and divergent sequences in closely related microbial genomes. Two *Enterococci* species were initially studied, *Enterococcus faecalis* (ATCC#19433) and *Enterococcus faecium*, (ATCC#19434). This technique can be used for many other species of microorganisms and types of environmental samples.

Enterococci are natural inhabitants of many animal gastrointestinal tracts, and are commonly found in sewage and animal waste. Enterococci are therefore frequently used as indicators of fecal pollution in environmental waters, and for human exposure risk assessments. These bacteria are also opportunistic pathogens, and cause nosocomial infections. The complete annotated genome of *E. faecalis* V. 583 and a draft genome assembly of *E. faecium* (Joint Genome Institute) are now available, allowing for an accurate post-assay assessment of the reported initial application of the Genome Fragment Enrichment (GFE) method.

Competitive DNA hybridization is used to select for chicken-specific DNA fragments. A total of 471 non-redundant chicken metagenomic sequences were retrieved and analyzed. All of these sequences were similar to prokaryotic genes, of which more than 60% could not be assigned to previously characterized functional roles. In general times, sequences assigned characterized functional roles were associated with cellular processes (11.7%), metabolism (11.0%) and information storage and processing (13.4%). Approximately 53% of the non-redundant sequences are similar to genes present in intestinal bacterial belonging to *Clostridia* (20.9%), *Bacteroidetes* (15.0%) and Bacilli (17.3%).

Twenty five sequences from the CP and CB clone libraries were selected to develop chicken fecal-specific PCR assays. These assays were challenged against fecal DNA extracted from 21 different animal species, including mammals and birds. The results from the host-specificity studies showed that twelve of the assays had a high degree of specificity to chicken feces. In addition, three assays were specific to chicken and turkey while another four assays tested positive to more than two avian species, suggesting a broader distribution of some of the enriched gene fragments among different avian fecal microbial communities. Fecal pollution signals were detected using chicken-specific assays in contaminated water samples, although the PCR assays showed different detection limits.

The competitive DNA hybridization approach to detecting chicken-specific fecal microbial sequences can rapidly select for numerous chicken fecal metagenomic regions that can be used as potential genetic markers for fecal source tracking.

Accurate identification of fecal pollution from particular animal species and individual sources is critical to assess associated health risks and to develop management plans to protect recreational water and preserve the integrity of drinking water sources (i.e., rivers and aquifers). In the United States, animal source identification methods are being applied in the development of Total Maximum Daily Loads (TMDL) as part of the Clean Water Act requirements, and in the evaluation of best management practices.

The present inventors have discovered that it is possible to prepare a set of species-specific DNA sequences utilizing GFE with total DNA extracted from fecal samples that provide the sequence information required to develop species-specific PCR primers for identifying the origin of animal fecal pollution in natural waters. The utility of these sequences was clearly demonstrated in a reduction to practice exercise in which three sequences were randomly chosen and used to design cow-specific PCR primers for detecting the presence or absence detection methods. These sequences, and the other sequences in the set for cows, are potential targets for developing PCR primers for presence or absence detection methods, real-time quantification of fecal sources, and microarray applications for risk assessment and risk management. This technique has also been applied to identify fecal contamination from chicken and human species, and to differentiate fecal pollution from these sources relative to cattle, horse, sheep, goat, pig, whitetail deer, Canadian goose, seagull, turkey, and other animals that potentially contribute to fecal pollution in a natural water source.

The present invention accelerates the identification of DNA sequences from one microorganism relative to another. For example, *Enterococcus faecalis*-specific DNA sequences were identified by using GFE to compare *E. faecalis* and *E. faecium* genomic DNA, and enrich for *E. faecalis* genome-specific DNA fragments. The two microorganisms compared, however, can be of any species, strain, or isolate if necessary.

Experiments conducted with Enterococci yielded 300 probable genome-specific sequences. Genome specificity was confirmed for 225 of these DNA sequences with a comparative sequence analysis using BLAST and BLAT algorithms. *E. faecalis* genome-specific sequences ranged from genes encoding phage related proteins to putative surface-exposed proteins, and even detected short regions of variation embedded in highly conserved rrn sequences. Thus, this method confirms the use of comparative genomics to recognize DNA loci that can be used as indicators of fecal pollution and to identify microorganism-specific genetic markers.

The present invention makes it possible, using molecular methods, to discriminate among clinically relevant species, to study the ecology of environmentally relevant microorganism species, and to identify microorganism-specific genetic markers for stress responses, virulence, carbon utilization, and cell-to-cell communication pathways.

Isolation of previously uncharacterized sequences from a microbial fecal community was made possible with the development of a DNA sorting method called Genome Fragment Enrichment (GFE). This technique is widely applicable to developing species and strain-specific PCR primers and probes, as well as to discovering novel virulence factors, use in computational toxicology, characterization of microbial communities, development of new exposure indicators, and development of methods for environmental monitoring of microbial water quality.

Genome Fragment Enrichment (GFE) uses competitive solution hybridization to obtain DNA fragments that are present in one pool of fragments but not another (as shown in FIG. 1). Labeled (e.g. biotinylated) sheared total genomic DNA from one bacterial species is first pre-hybridized with genomic DNA fragments from a second species (blocked), prior to being self-hybridized with PCR-amplified DNA fragments from the original source that contain defined terminal sequence tags (PCR primer sites). There are many conventional methods for adding defined terminal sequence tags to DNA, and any one of these methods can be used in the present invention. The DNA hybrids obtained are then isolated by binding with the label, for example biotin label binds with streptavidin, and the desired captured genomic DNA strands are then re-amplified by PCR. Thereby, DNA sequences unique to the first pool are enriched, and can be identified by subsequent cloning into *Escherichia coli* plasmids and DNA sequencing.

To identify DNA targets for microbial source tracking (MST), a metagenomic approach was used (that is, compared DNA pools were from total fecal microbial community DNA). The technical challenge was to determine a way to simultaneously compare thousands of genomes isolated from fecal samples, and identify discriminatory DNA sequences from microorganisms that have not previously been cultured or characterized.

In an initial metagenomic application of the invention, cow-specific sequences were obtained by comparing the metagenomic DNA extracts derived from cow and pig fecal samples using genome fragment enrichment (GFE). GFE uses solution phase competitive nucleic acid hybridization to achieve enrichment for target molecules, as does the second step in the previously described RNA-based method for analysis of microbial gene expression Selective Capture of Transcribed Sequences (SCOTS) (Graham et al., 1999, PNAS 96:11554-11559). SCOTS allows for the selective capture of bacterial cDNA molecules from total cDNA prepared from infected cells or tissues in a first step, using hybridization to biotinylated, bacterial, genomic DNA. These are previously well-described nucleic acid manipulation methods that are applied differently in each analysis method. Major key changes were required to use competitive nucleic acid hybridization for the DNA analysis method invented, Genome Fragment Enrichment.

Fundamental differences between SCOTS and GFE are that GFE identifies regions of DNA variation, rather than differentially expressed genes (as RNAs). In addition, significant differences are present in the tagging process that adds PCR primer sites to genome fragment termini, in preparation of the capturing and blocking DNA fragment pools, and metagenomic GFE applies to a larger range of DNA fragments both in size (150 bp to 1200 bp) and sequence composition (entire genomes and metagenomes). GFE is also substantially different from the currently available SSH genome subtraction method. Unlike SSH, GFE enriches for variable DNA segments using a positive physical selection process. Target DNA segments are isolated by, for example, streptavidin binding and removed from solution, washed, and eluted in a separate reaction. All target DNA strands obtained are then amplified by complementary single-primer PCR (Grothues et al., 1993; *NAR* 21: 1321-1322). SSH attempts to enrich by an unequal or biased PCR amplification itself, relying on self-complementary terminal regions to suppress amplification of molecules common to both comparison pools. Such PCR-mediated approaches are subject to inherent variability in the PCR process itself, and are not the basis for selecting desired target molecules in GFE.

Gene Fragment Enrichment (GFE) differs from previously known techniques in a variety of ways. SCOTS is a gene expression analysis method, while GFE is intended to determine the differences between microbial genomes and total environmental DNA samples. These approaches are also based on analysis of fundamentally different types of nucleic acids. For example, SCOTS requires the use of difficult RNA extraction methods and reverse transcriptase to make cDNA. This cDNA must then be sorted into bacterial and host nucleic acids by hybridization without competitor other than bacterial rDNA containing plasmid DNA. In GFE, target DNA is first extracted, then sheared by sonication, randomly primed with a Klenow DNA polymerase I reaction, and then amplified by lone-primer-PCR (Grothues et al., 1993; *NAR* 21: 1321-1322). These are just a few of the differences in these two entirely different procedures.

SCOTS also first requires three initial rounds of selection without blocking competitor in order to obtain the microbial component of cDNA from infected cells or tissues and to normalize the representation toward unit gene copy number. The blocking component of GFE is sheared native microbial DNA, while the blocking cDNA used in the subsequent SCOTS cDNA enrichment are PCR amplicons amplified from a cDNA pool. Unlike SCOTS, GFE has no procedural step or goal to normalize sequences to unit copy number, and there is no need to separate nucleic acids from the host and microbe.

SH is an optimization of Representational Difference Analysis or RDA (Lisitsyn et al. 1993). RDA relies on the difference in amplification efficiency of DNA containing two flanking PCR primer sites (exponential amplification) relative to a single site at one end (linear amplification). By hybridization of DNA strands from two pools of DNA fragments with different linker sequences, those DNA strands from the first pool that are not able to hybridize with strands from the second pool reassociate, and form superior templates for exponential PCR amplification. Hetero-hybrids that form from the annealing of complementary strands from shared DNAs in both pools have only one flanking primer target site, and those that are unique to the second pool do not have any flanking primers sites. Differential amplification of reassociated strands unique to the target pool is then achieved by their exponential increase in a subsequent polymerase chain reaction (PCR). The first is then used to obtain amplified material unique to the first nucleic acid pool. GFE, in contrast, is a physical separation process that relies on competitive hybridization to physically separate nucleic acids prior to PCR amplification (i.e., positive selection process). SH is a PCR mediated selective process, while GFE is a physical separation method followed by an amplification step.

Subtractive hybridization (Straus and Ausubel, 1990; PNAS 87:1889-1893) is a different physical nucleic acid separation process, and relies on the inherently difficult goal of removing all of the common DNA strands from two nucleic acid pools by hybridization (negative selection process). DNA from one source is modified for later selective binding, and is then hybridized with material from a second source. Multiple rounds of hybridization and binding are then used to physically deplete the second pool of all complementary DNA strands. This is a different process from that used in GFE in that it is a negative hybridization and removal process. In contrast, GFE uses a positive selection approach to sample only those nucleic acids that are still able to bind complementary DNA strands in the presence of a competitor from a second source. Unlike these other approaches it does not rely on removing all of the complementary sequences in two nucleic acid pools, as does subtractive hybridization. GFE is therefore inherently less prone to obtaining "false positive" or shared sequences left behind by incomplete subtractive approaches like SSH, RDA, and subtractive hybridization.

The GFE technique thus provides a method for identifying differences between communities of microorganisms. This process includes the following steps:

a. obtaining labeled first genomic DNA fragments from a first community (of microorganisms) in a sample and hybridizing the first genomic DNA fragments with second genomic DNA fragments from a second community of microorganisms;

b. incubating the first and second genomic fragments with additional genomic fragments from the first community of microorganisms containing defined terminal sequence tags to form DNA hybrids;

c. capturing the resulting DNA hybrids formed with tags and PCR amplification of only the tagged fragments;

d. obtaining enriched amounts of sequences unique to the first community of microorganisms; and e. identifying the enriched sequences.

This process can be used for any microorganisms present in a sample. The sample may originate from any animal suspected of contributing to contamination of a stream or waterway, including but not limited to cattle, fowl, pigs and humans.

The primers can be modified easily using conventional software such as PRIMER EXPRESS from ABI. To modify a primer using this software, one enters the DNA sequence and designates a primer location based on data from the conventional PCR primer. The program then designs a new primer sequence that is modified to work on a real-time platform.

Alternatively, one can modify primer sequences by hand. The key information required is the DNA sequence. It is helpful to have the conventional PCR data to designate where, the 3' end of the primers should be situated.

Streptavidin is used merely as an illustration of modifying and binding partners that can be used. Any suitable chemical tagging and binding technology will work with GFE.

Figure 2:
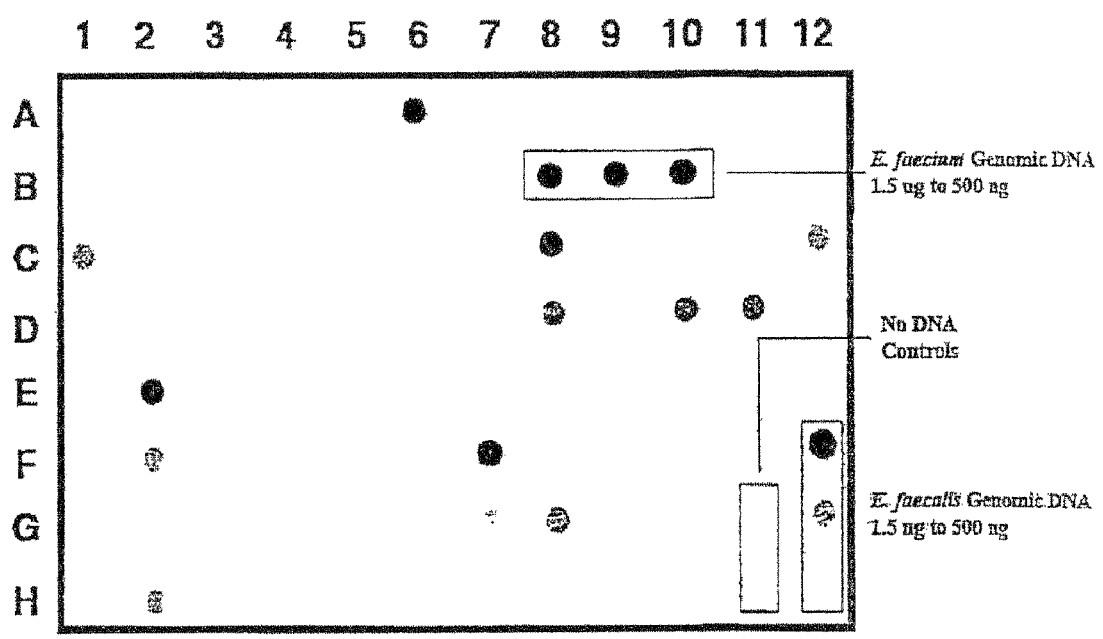

FIG. 2 shows the result of dot blot hybridization analysis of candidate *E. faecalis* (ATCC #19433) specific DNA fragments. PCR amplicons from all non-redundant clone sequences (88 shown) were transferred to nylon membranes with a dot blot manifold and hybridized to biotin labeled *E. faecium* (ATCC #19434) genomic DNA. Positive controls include 1.5µ (row B, column 8), 1 µg (row B, column 9 and 500 ng) (row B, column 10), of *E. faecium* genomic DNA. The *E. faecium* genomic DNA cross-hybridized with 1.5 µg (row F, column 12), and 1 µg (row H, column 12), no DNA controls (rows G and H, column 11) did not hybridize to probe.

Figure 3:
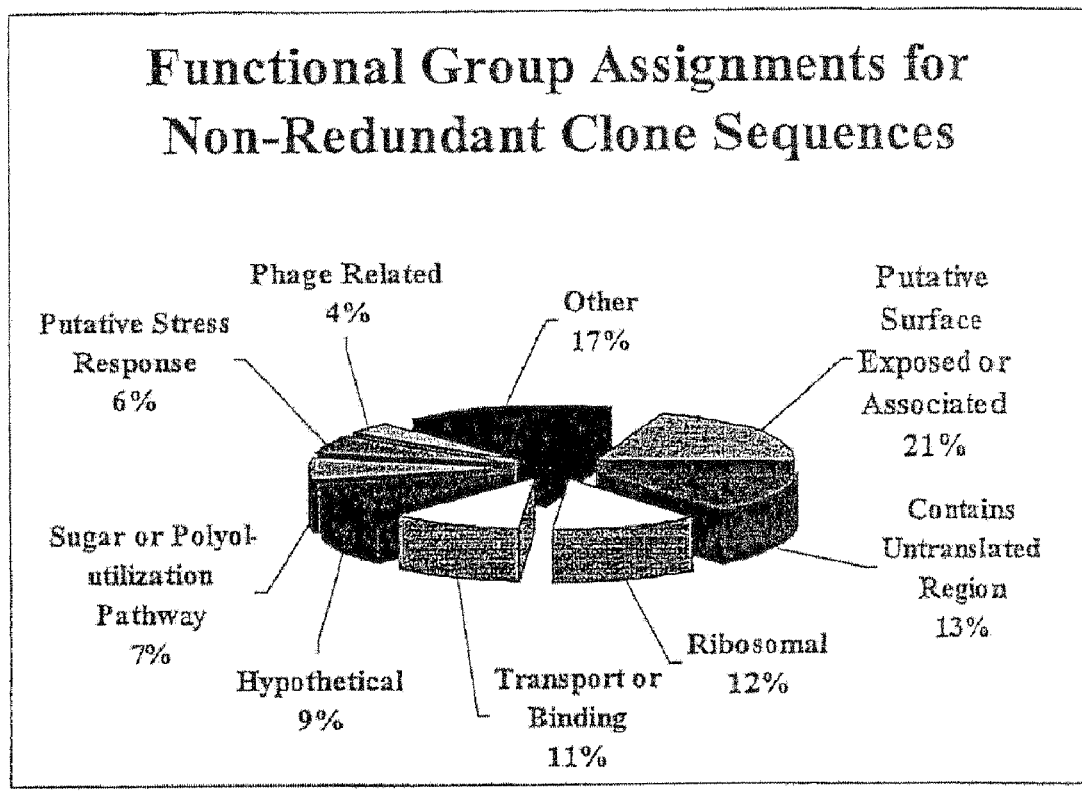

FIG. 3 shows functional group assignments for non-redundant clones.

FIGS. 4A-C illustrate the limitation of detection for host-specific primer sets using serial dilutions of cow fecal metagenomic DNA.

FIG. 4A shows that 1 fg or DNA was detected for Marker 1 (Bac1F & Bac1R).

FIG. 4B shows 10 fg of DNA was detected using Marker 2 (Bac2F & Bac2R).

FIG. 4C shows that 0.1 fg or DNA was detected with Marker 3 (Bac3F & Bac3R).

Figure 5:
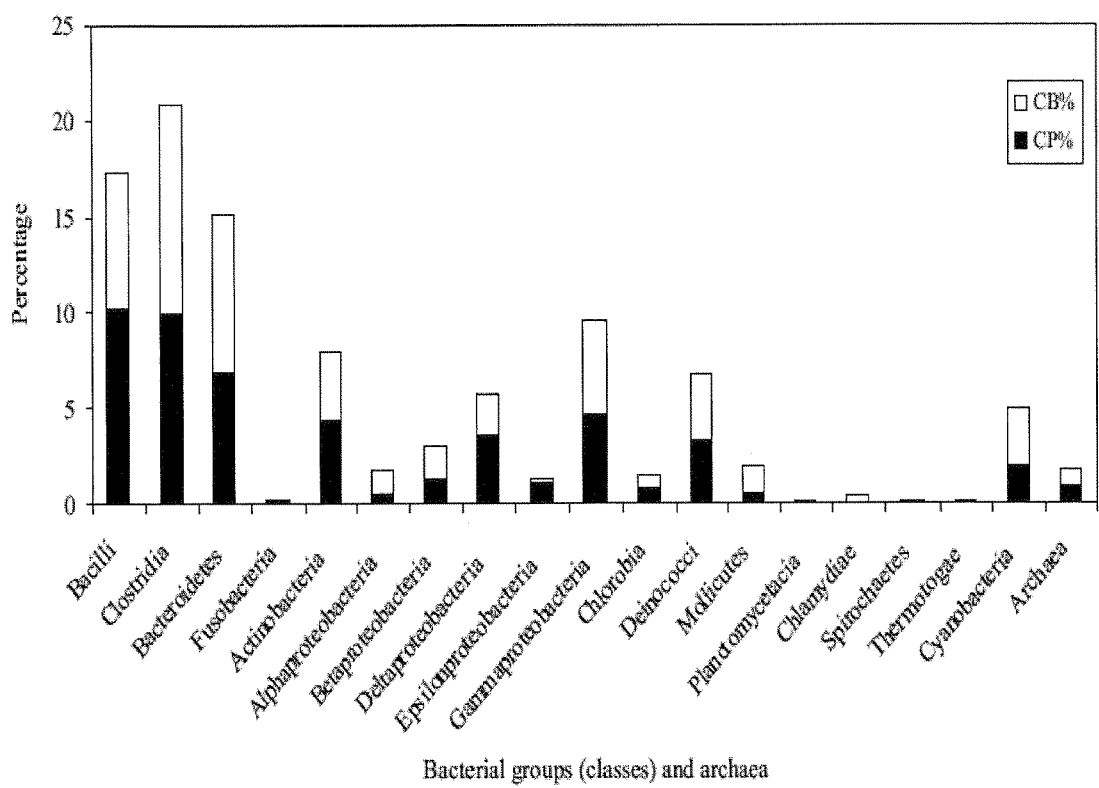

FIG. 5 is a schematic representation of the DNA enrichment method used to select for chicken and avian fecal community DNA sequences. Two experiments were performed using biotin-labeled, sheared chicken fecal metagenomic DNA (tester DNA). In one experiment, tested RNA was challenged against metagenomic DNA fragments from porcine fecal DNA extracts (CP). In a separate experiment, tester DNA was challenged against metagenomic DNA fragments from a bird composite DNA fecal extract (CB). DNA hybrids were isolated by streptavidin binding. Clone libraries were developed and randomly selected clones were sequenced to determine their potential protein function.

Figure 6:
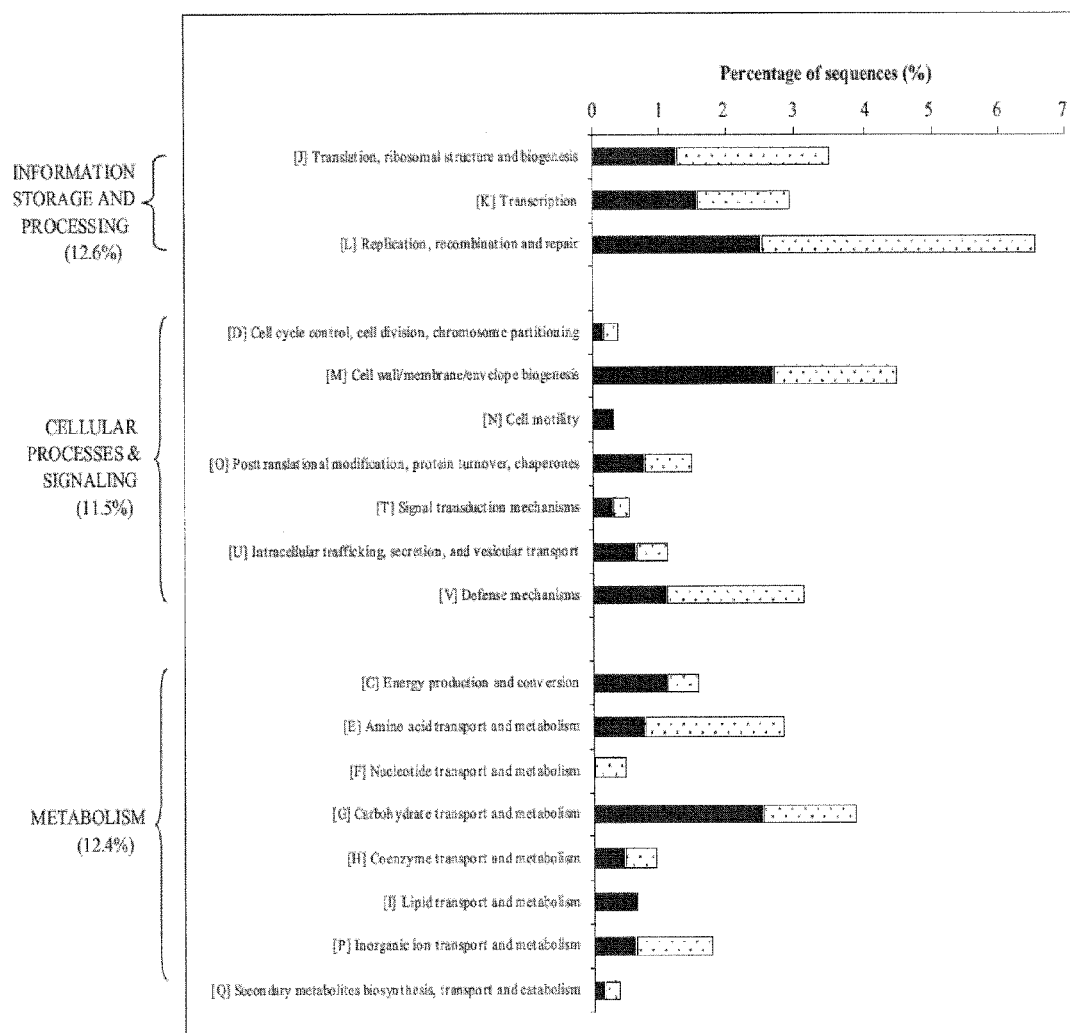

FIG. 6 shows the function annotation of enriched chicken fecal DNA sequences (COG classification of top BLASTX hit; E-value≦10$^{-3}$; n=471). CP clones are represented by open bars, while CB clones are represented by solid bars, total 18% chicken fecal DNA versus the fecal DNA of turkey, seagull, and Canadian goose. Not included in this figures are the dines associated with poorly characterized categories (31% and 32% in CP and CB clone libraries, respectively).

FIG. 7 shows gel electrophoresis of PCR products from reactions with chicken-specific PCR assays CP8, CP20 and CB42 (panels A, B and C, respectively). Each PCR assay was tested against an individual DNA extract from possible fecal-contaminated water by human (waste water, OH, lane 1); cow (creek, NE, lane 2); pigs (pond, OH, lane 3); geese (ponds, NJ, lane 4) and chickens (creek and lagoon, GA, lanes 5 and 6); river, DE; lanes 7-12. Lanes 13 and 14 are the PCR reaction controls for negative and positive.

DETAILED DESCRIPTION OF THE INVENTION

Genome Fragment Enrichment

Genome fragment enrichment is useful in identifying regions of genetic variation between two microbial genomes or metagenomes of entire bacterial communities such as microbiota present in fecal material from different animal species. For microbial genome comparisons, genome fragments from one microbial species are first hybridized with genomic DNA fragments from a second microbial species, and then these fragments are incubated with additional genomic DNA fragments from the first species containing defined sequence tags. The resulting DNA hybrids are captured, and all of the captured strands from the tagged pool are PCR amplified by primers complementary to the added terminal tag sequences. These amplified DNAs are sequences unique to the first microbial species or source. Sequences obtained are then unambiguously identified by cloning into *E. coli* plasmids and DNA sequencing.

Figure 1:
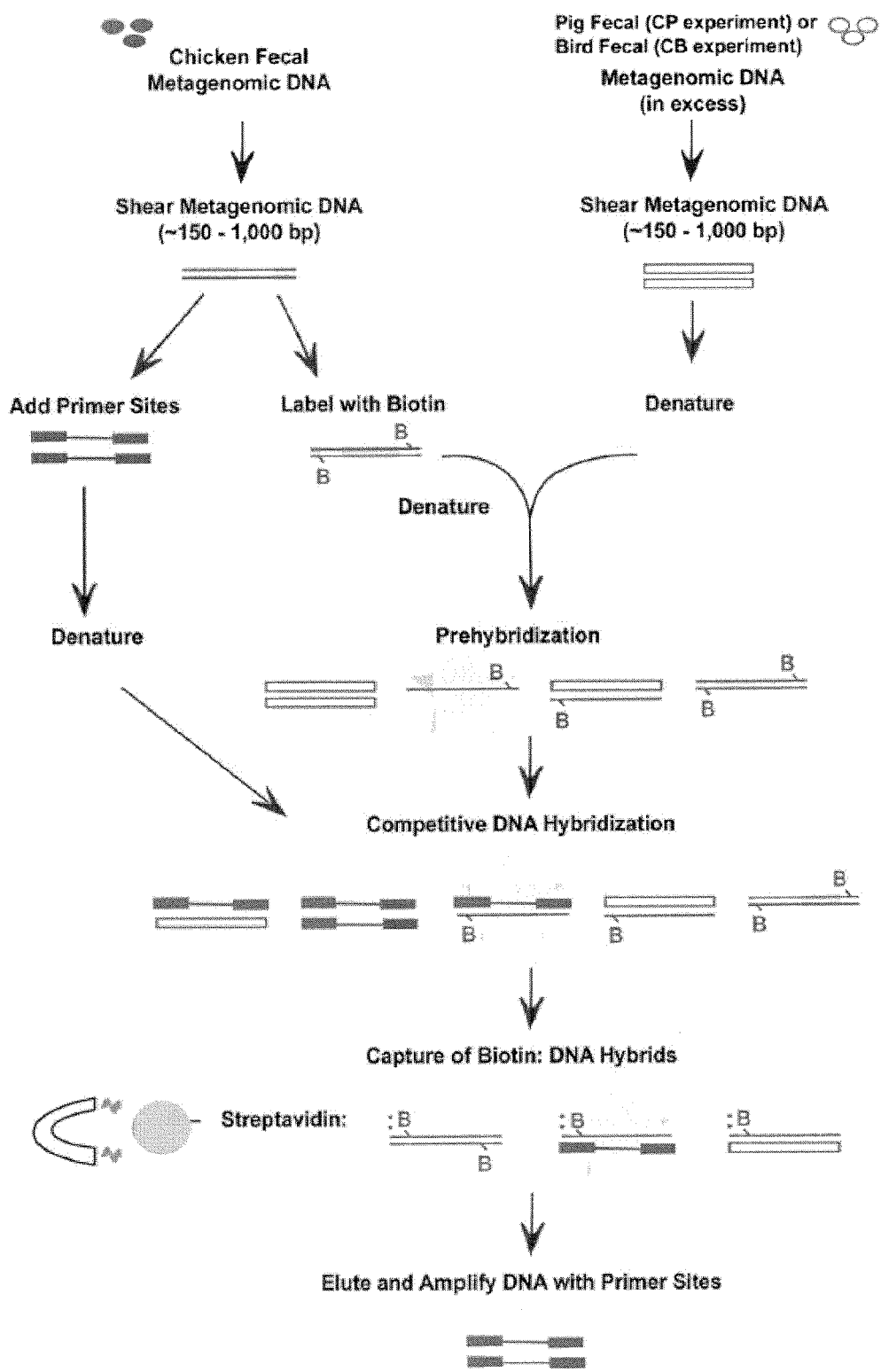
FIG. 1 illustrates a process for identifying *E. faecalis* (ATCC #19433) DNA sequences that are absent or significantly divergent (~70%) in the *E. faecium* (ATCC #19434) genome using GFE. Biotin-labeled genomic DNA fragments from one *E. faecalis* are first hybridized with genomic DNA fragments from *E. faecium* (blocked), prior to incubation with additional genomic DNA fragments from the original source containing defined terminal sequence tags. By capturing the resulting DNA hybrids with streptavidin and PCR amplification of only the tagged fragments, DNA sequences unique to *E. faecalis* are enriched, and can be unambiguously identified by subsequent plasmid cloning and DNA sequencing.

Genome Fragment Enrichment uses a competitive hybridization process that is also a part of the previously described RNA analysis method, SCOTS (Graham et al., 1999). As seen in the second stage of SCOTS, GFE uses competitive solution hybridization to obtain DNA fragments that are present in one pool of fragments but not in another (FIG. 1). However, unlike SCOTS, GFE targets regions of chromosomal variation, rather than differently expressed genes. Labeled sheared total genomic DNA from one bacterial species is first pre-hybridized with genomic DNA fragments from a second species (blocked), prior to being self-hybridized with PCR-amplified DNA fragments from the original source that contain defined terminal sequence tags. DNA hybrids are then isolated by, for example, streptavidin binding or any conventional chemical tagging and binding method, and the captured genomic fragments are re-amplified by PCR. Thereby, DNA sequences which are unique to the first pool are enriched and can be identified by subsequent plasmid cloning and DNA sequencing.

Genome fragment enhancement was successfully used to identify hundreds of DNA sequences which are either absent or divergent in one bacterial genome compared to another, as well as microbial cow-specific DNA sequences present in a cow fecal metagenome and absent in a pig metagenome. In addition to cow-specific DNA sequences, GFE has been successfully applied to isolate microbial human-specific and chicken-specific DNA sequences. This technique can also be used to identify DNA sequences either absent or divergent in a variety of bacterial genomes or microbial communities (i.e. fecal samples). Specific non-limiting examples of animals include bovine, human, and avian.

Host-specific primer sets developed from DNA sequences isolated with GFE can be used for end point and real-time PCR applications, as well as microarray applications to make species-specific identifications. Conventional host-specific primer sets can readily be modified to provide real-time PCR primers. Specific non-limiting examples of animals reported herein include cattle, human, and chicken.

Materials and Methods

Sample Collection and DNA Extraction

Fecal samples were collected from diverse geographic locations in the United States (Florida, New Jersey, West Virginia, Delaware, Ohio, Texas, Nebraska and Georgia) and from one location in the Republic of China (Shandong). Samples from the following animals were used to test the host specificity and host distribution of the potential host-specific markers: *Sues scrota* (pig), *Capra agars* (domestic goat), *Ovis aries* (sheep), *Equus caballus* (horse). *Bos Taurus* (bovine), *Gallus gallus* (chicken), *Meleagris gallopavo* (turkey), *Anser* sp. (Canadian goose), *Larus californicus* (seagull), *Treron* sp. (pigeon), *canis latrans* (coyote), *Scirus carolinensis* (gray squirrel), *Odocoileus virginianus* (whitetail deer), *Didelphis virginiana* (possum), *Canis familiaris* (dog), *Felix catus* (cat), *Lynx rufis* (bobcat), *Procyon lotor* (raccoon), *Erinaceus* sp. (hedge hog), *Loragyps stratus* (black vulture) and *Homo sapiens* (human). These are shown in Table 1.

TABLE 1

Fecal and water samples used to test host specificity and host distribution

| Test type[a] | Animal type, sampling location | Number of samples[b] |
|---|---|---|
| Host specificity (composite samples) | Pig, DE | 10 (2) |
| | Cow, WV | 17 (3) |
| | Cow, DE | 11 (1) |
| | Human, WV | 16 (3) |
| | Goat, DE | 10 (2) |
| | Sheep, DE | 11 (3) |
| | Horse, WV | 5 (1) |
| | House cat, WV | 11 (1) |
| | Domestic dog, WV | 13 (1) |
| | Deer, WV | 6 (1) |
| | Coyote, TX | 10 (1) |
| | Squirrel, TX | 4 (1) |
| | Possum, TX | 2 (1) |
| | Seagull, WV | 8 (1) |
| | Canadian goose, WV | 16 (1) |
| | Turkey, DE | 11 (1) |
| | Turkey, OH | 6 (1) |
| | Pigeon, WV | 2 (1) |
| Host specificity (individual samples) | Turkey, WV | 11 |
| | Turkey, OH | 7 |
| | Turkey, China | 4 |
| | Duck, FL | 1 |
| | Duck, GA | 25 |
| | Duck, China | 9 |
| | Pigeon, WV | 2 |
| | Pigeon, China | 5 |
| | Goose, GA | 27 |
| | Goose, WV | 21 |
| | Goose, NJ | 2 |
| | Seagull, FL | 8 |
| | Seagull, DE | 3 |
| | Seagull, GA | 13 |
| | Cow, WV | 9 |
| | Human, WV | 13 |
| | Pig, DE | 9 |
| | Black vulture, TX | 1 |
| | Racoon, TX | 1 |
| | Hedgehog, WV | 1 |
| | Bob cat, TX | 1 |

TABLE 1-continued

Fecal and water samples used to test host specificity and host distribution

| Test type[a] | Animal type, sampling location | Number of samples[b] |
|---|---|---|
| Host distribution | Chicken, DE | 12 |
| | Chicken, WV | 15 |
| | Chicken, OH | 9 |
| | Chicken, GA | 4 |
| | Chicken, China | 30 |
| Fecally impacted water samples | Possibly chicken water, GA | 2 |
| | Possibly chicken water, DE | 6 |
| | Possibly goose water, NJ | 9 |
| | Possibly human water, OH | 5 |
| | Possibly cow water, NE | 20 |
| | Possibly pig water, OH | 2 |

[a]Different tests were performed to validate the host-specific assays. DNA extracts from fecal samples were used to test host specificity using composite as well as individual fecal samples. To determine host distribution of genetic markers DNA extracts from individual chicken fecal samples were used. DNA extracts from water samples were used to determine the presence of host specific markers in fecally impacted water bodies.
[b]Numbers in parentheses represent the number of composites used in each particular case. For example, DNA extracts from two sets of five different fecal samples were combined to create the two composites tested in host-specificity studies.

Feces were collected aseptically, placed into sterile conical tubes with screw caps, and stored at −80° C. until required. Total DNA was extracted from the fecal samples using the Mo Bio Fecal kit (Mo Bio Laboratories, CA) or the FastDNA Kit (Q-Biogene, Carlsbad, Calif.) following the protocols provided by the manufacturers. Total DNA was eluted in 50 or 100 microliters of molecular grade water, and DNA concentrations were measured using a NanoDrop® ND-1000 UV-Vis Spectrophotometer (Nanoprop Technologies, Inc., Berlin, Germany, using 2 microliters of each DNA extract.

Water samples that were possibly contaminated by chickens (Georgia), Canadian geese (New Jersey), cow (Nebraska), pig (Ohio) and human (Ohio), shown in Table 1, were collected in sterile bottles and transported to the laboratory in ice coolers. Samples of 100 ml were filtered onto 47 mm polycarbonate membranes (0.2 micron pore size, Millipore corporation, MA). The membranes were then transferred into sterile conical tubes and kept at −80° C. until further processing. DNA from water samples was extracted using the FastDNA Kit.

Genome Fragment Enrichment of Chicken Fecal DNA Versus Other Fecal DNA

A modification of the GFE method developed by Shanks et al. was used to enrich for chicken-specific metagenomic regions, shown in FIG. 5. Briefly, genomic DNA extracts from individual chicken fecal samples were mixed to create a fecal microbial community DNA composite, which was designated "tester." A similar approach was performed for the DNA extracts of other animals that were used as "blocker." The term tester is used as the pool of metagenomic DAN from which the markers are selected, while the term blocker is used as the pool of DNA that is used to block the sequences that are in common with the tester DNA. In the original GFE protocol, DNA extracts from only one individual were used as tester and blocker. A composite DNA pool (n=14 for chicken; n=9 for pig) was used so as better to represent the diversity of host metagenomes of both tester and blocker and thus decrease the potential assay cross-reactivity. Additionally, a smaller amount of tester and blocker was used in this study, and the tester-blocker ratio was 1:15. DNA purification steps were performed using isopropanol precipitation rather than ethanol precipitation in order to improve the recovery yields. Washing steps after the competitive DNA hybridization steps were also modified to increase stringency.

Two independent GFE experiments were performed. In the first experiment, a composite of chicken metagenomic DNA (tester) and a composite of pig metagenomic DNA (blocker) were used to enrich for chicken-specific fragments. This experiment was labeled CP. In order to selectively retrieve fragments from the chicken fecal metagenome, a subsample of the tester DNA was labeled with biotin and used as a capturing surface. To prepare the DNA capturing surface, approximately 10 micrograms of composite fecal DNA from 14 different chickens from West Virginia (714 ng per individual fecal sample) were mechanically sheared into approximately 100-900 base pair (bp) fragments and labeled with biotin. Ten micrograms of a DNA extract composite from nine pigs was used to prepare the blocker solution. To prepare DNA sued to enrich for host-specific fragments, sequence-specific oligonucleotide primers having both a common 5' sequence and nine random residues (herein called K9 primers; gacactctcgagacatcaccggtacc-nnnnnnnnn) were linked to 1 microgram of sheared chicken fecal DNA, using Klenow polymerase extension. Metagenomic fragments modified with the K9 primers are herein described as K9-tagged DNA.

The second GFE experiment, labeled CB, was conducted again using chicken metagenomic DNA as the tester, which a composite of metagenomic DNA from different birds (n=35; 11 turkeys, 16 Canadian geese and 8 seagulls) was used as the blocker. The blocker fecal DNA was prepared by mixing equal amounts of DNA for each animal type to reach a total of 10 micrograms of composite DNA.

In both GFE experiments, the pre-hybridization solution was prepared by mixing 100 nanograms of the genomic DNA capturing surface and 1.5 micrograms of the blocker DNA solution overlaid with mineral oil. The solution was heated at 98° C. for two minutes before 4 microliters of 5 M NaCl was added. The mixture was allowed to pre-hybridize for 20 minutes at 55° C. The tagged K9-tagged chicken genomic DNA (1090 ng) was incubated separately at 98° C. for two minutes and mixed with 4 microliters of 5 M NaCl before it was transferred to ice. The entire K9-tagged fecal DNA solution was added to the pre-hybridization solution and was incubated overnight at 55° C. The conditions of the pre-hybridizations and hybridizations in the two experiments for CP and CB were the same. DNA hybrids were isolated by streptavidin binding and the captured K9-tagged genomic fragments were amplified by lone-linker PCR. All PCR reactions were performed using a MJ Research DNA Engine Tetrad 2 thermal cycler (Bio-Rad, Hercules, Calif.). In each case, PCR products from the previous round were used for the next enrichment round. Each experiment was conducted in triplicate using the same preparations of capturing surface, blocking, and tester DNAS. PCR products from five reactions, for each enrichment round, were pooled and cloned into pCR4.1TOPO following the manufacturer's instructions (Invitrogen). Cloning libraries if enriched fragments were developed for rounds 1 and 2 of the CB experiment and for round 2 of the CP experiment.

Sequencing and Data Analysis

Individual clones were grown in Luria Broth plus ampicillin as the selected agent, and cells were then added directly to M13-PCR assays to screen for inserts. PCR assays (@5 microliters) contained 1× ExTaq PCR buffer (Panvera), 2.5 mM (each) of dATP, dCTP, dGTP and dTTP; 0.2 microM of M13F and M13R primers; 0.064% bovine serum albumin (Sigma-Aldrich); 0.625 U ExTaq; and 1 microliter of cells.

Amplification conditions included an initial incubation at 94° C. for three minutes followed by 20 cycles of 94° C. (30 s), 52° C. (20 s) and 72° C. (40 s). Inserts were confirmed using agarose gel electrophoresis, and PCR products were purified using Qiaquick 96 plate (Qiagen). Sequencing was carried out using Big Dye terminator chemistry and capillary gel electrophoresis (Applied Biosystems PRISM 3730XL DNA Analyzer) at the Cincinnati Children's Hospital Medical Center Genomics Core Facility (Cincinnati, Ohio). Sequences were generated for each clone using M13 forward and reverse primers. Sequence editing and alignment were performed using Sequencer software (Gene Codes Corporation, Ann Arbor, Mich.). The putative protein transcript of each sequence was annotated based on the biochemical function of similar gene sequences using BLASTX with the non-redundant (NR)/GenBank database. BLASTX sequence matches with E values of $\leq 10^{-3}$ and sequence identities of $\geq 30\%$ were considered to be similar protein sequences. To organize sequences into functional gene categories, the DNA sequences were grouped according to the database of Clusters of Orthologous Groups (COG) of proteins. Enriched sequences were assigned bacterial class annotations based on the top BLASTX hit (lowest E-value score (GenBank NR database.

Primer Design and PCR Tests

Primers were designed using Premier Designed software (version 2.01; Cary, N.C.) under the following conditions: no hairpin, no primer dimmer formation, and annealing temperature of 54 or 65° C. Assays were optimized through temperature gradients using various concentrations of fecal DNA templates. Primers were tested for host specificity against fecal DNA composites for each animal type listed above. The primers that showed host specificity to chicken composites were further challenged against fecal DNA extracts from individual cow, human, pig, turkey, Canadian goose, seagull, duck and pigeon specimens (Table 1). Host-specific assays were used to measure host distribution of each genetic marker with individual chicken fecal samples. In addition, selected chicken fecal-specific PCR assays were challenged against DNA extracted from water samples presumed to be impacted with chicken fecal contamination. PCR assays specific to *Bacteroidetes* spp. and *Clostridium coccoides* were used to determine the presence of potential PCR inhibitors in all DNA extracts and for the potential presence of fecal pollution in water samples. A positive signal from the general *Bacteroides* spp. and *C. coccoides* assays in samples that tested negative for the host-specific assays was used as evidence for the absence of PCR inhibition. All tests were performed using two DNA concentrations including 1 and 10 nanograms/microliter for host-specificity studies, DNA from each fecal sample was first extracted and then equal amounts of each DNA extracts were mixed to create fecal DNA composites. To test host distribution, individual DNA extracts from each targeted animal were tested. The presence of PCR products was visualized using 2% agarose gel electrophoresis and GelStar as the nucleic acid stain (FMC Bioproducts, Rockland, Me.).

Analysis of GFE Sequences

A total of 471 clones were characterized in this study, 196 from the CP experiment (chicken fecal DNA versus pig fecal DNA) and 275 from the CB experiment (chicken fecal DNA versus a composite containing turkey, seagull and geese fecal DNA). Eighty sequences did not have significant similarity to sequences in the NR protein database. Based on top BLASTX hits, the analyzed sequences were similar to genes encoded in 19 bacterial groups (classes) and Archae. *Clostridia*-like sequences were the most abundant group (20.9%), with many sequences showing the greatest similarity (top BLASTX hit based on E-values) to *C. perfringens, C. tetani, C. thermocellum* and *Moorella thermoacetica* proteins, as shown in FIG. 6.

Bacilli-like sequences were the second most abundant group (17.4%), with sequences similar to members of the genera *Enterococcus, Lactobacillus,* and *Streptococcus*. *Bacteroides*-like sequences represented 15.1% of the total clones analyzed, with sequences showing similarity to *Bacteroides* spp., *Cytophaga hutchinsonii,* and *Porphyromonas gingivalis*. Other sequences showed similarity to proteins from *Actinobacteria* (8.0%) and *Cyanobacteria* (4.9) and to α-(1.8%), β-(3.1%), γ-(9.5%) and δ-Proteobacteria (5.8%). A few sequences (1.7%) showed similarity to archael sequences. Interestingly, some of the sequences partially matched pathogenic bacterial genes, such as *E. coli* (93-100% identity), *Listeria monocytogenes* (84% identity), *Salmonella enterica* (96-100% identity), and *Shigella flexneri* (87-100% identity). Although the sequences in the NR database is biased toward cultural microorganisms, bacterial class designations were made to obtain an idea of the diversity of bacterial populations associated with the enriched DNA libraries.

The abundance of *Clostridia-* and Bacilli (mainly *Lactobacilladales*)-like proteins in the metagenomic libraries is not surprising in light of findings from 16S rDNA-based studies indicating that *Clostridia* and *Lactobacilladales* represent approximately 65% and 23%, respectively, of the intestinal (cecum) bacterial community of broiler chickens. In contrast, *Bacteroidetes* are not as numerically dominant as *Clostridia* and Bacilli in chickens as in other gut systems (e.g., humans), the results obtained further confirm that as a group *Bacteroidetes* possess a high number of bacterial host-specific genes, some of which might be involved in host-microbial interactions. In addition, these results further confirm the high selection process of the GFE technique.

Other gut bacteria represented in the GFE libraries and commonly identified in 16S rDNA gut libraries are *Bifibacterium* spp., *E. coli, S. Enterica,* and *Campylobacter* spp. Some clones in the GFE library are similar to genes found in environmental bacteria like *Arthrobacter* spp., *Cornebacterium* spp., *Pseudomonas* spp. and *Geobacter* spp. These organisms might be transitory in the gut and therefore similar sequences would not be good candidate genes for chicken-specific PCR assays.

Most fragments in the top BLASTX sequence match showed significant similarity to a *Bacteriodetes* protein frequently showed similarity to the same protein in other *Bacteroidetes* species, suggesting that some of these genes could be playing important roles in this bacterial group. In contrast, in several cases when the sequence matched *Clostridia* or Bacilli proteins, other potential matches suggested a link to proteins from other organisms, including *Paracoccus denitrificans, Cornebacterium efficient, Trichodesmium erythraeumi* and *Chlamydophila pneumoniae*. Altogether, these data suggest that *Clostridia* and *Lactobacillus* genes similar to non-fecal bacterial genes might not be good candidates for the development of host-specific PCR assays.

Most fragments in which the top BLASTX sequence match showed significant similarity to a *Bacteriodetes* protein frequently showed significant similarity to the same protein in other *Bacteroidetes* species, suggesting that some of these genes could be playing important roles in this bacterial group. In contrast thereto, in several cases when the sequence matched *Clostridia* or Bacilli proteins, other potential matches suggested a link to proteins from other organisms, including *Paracoccus denitrificans, Corynebacterium effi-* cients, *Trichodesmium erythraeumi*, and *Chlamydophilia pneumoniae*. Altogether, these data suggest that *Clostridia* and *Lactobacillus* genes similar to non-fecal bacterial genes might not be good candidates for the development of host-specific PCR assays.

In both CP and CB libraries, more than 60% of the bacterial clones were similar to poorly characterized genes (e.g., 63.9% were predicted as genes with unknown functions). Sequences similar to *clostridia* had the largest proportion of enriched fragments associated with uncharacterized functions (56.6%), while *Bacteroidetes* and Bacilli had a smaller proportion (30.6% and 45.6%, respectively). Of the fragments associated with characterized function genes (36.1% of total analyzed sequences). 55, or 11.0% of the sequences were associated with metabolic process and 63, 13.4%, sequences were associated with information storage and processing (e.g., DNA repair and DNA replication), shown in FIG. 7. Sequences with high similarity to characterized genes from *Bacteroides, Clostridia* and Bacilli were used for PCR assay development, as shown in Table 2.

TABLE 2

Description of primers tested for host specificity

| Clone # | Fragment size/PCR product size (DNA bp) | Forward and reverse primer sequences (5'→3') | SEQ ID NO. | COG category | Top BLASTX hit organism (lowest E value) | Expect values | Amino acid Sequence length (%identity) | Primer specificity |
|---|---|---|---|---|---|---|---|---|
| CB-R2-10 | 326/306 | CCATCCACAGCACGTCGT AAGATCTTCATCCAGTAC GGCA | 40 | Cellular processes (chaperones) | *Bacteriaroides fragilis* | 4E-27 | 108 (50) | Chicken and goat |
| CB-R2-27 | 614/607 | CGAAGCGGAGAAGAACAA GAGTTCCGCAACGTAGAG GAAA | 41 | Metabolism (inorganic ion) | *B. thetaiotoo-micron* | 2E-44 | 205 (45) | Chicken, goat, and sheep |
| CB-R2-28 | 344/327 | GGCAAGCCTCAATCGCA TGTTCTGGTCGTTGGGC TGA | 42 | Cellular processes (signal transduction) | *B. fragilis* | 3E-35 | 115 (61) | Chicken and sheep |
| CB-R2-34 | 418/261 | CTCCAGGATTTCGTGGG AAAGGAGCAGCTGACGG CA | 43 | Information storage and processing | *Clostridium thermocellum* | 5E-26 | 115 (52) | Chicken, pigeon, and sheep |
| CB-R2-42 | 627/265 | GACGAGATCTATATTTG CCTCACGGAGCATATCC TACGATCA | 44 | General function predition only | *Desulfito-bacterium hafniense* | 1E-03 | 93 (33) | Chicken |
| CB-R2-80 | 589/287 | CGTGAATTTCCGCTAC TGACCCTTCCTTGCGT CCCA | 45 | Cellular processes (wall/membrane) | *B. fragilis* | 1E-25 | 125 (45) | Chicken |
| CP1-1 | 623/281 | GGCAGGCATCAAGTCAAC ATGGCAAAAGCAACTGTC ATGGCA | 46 | Cellular processes (cell division) | *C. tetani* | 3E-16 | 99 (41) | Chicken and other birds |
| CP-1-10 | 383/350 | AGGAGCATTTGTCGCCCT AGGTAAAGCTGCCCGGTA ATA | 47 | Cellular processes (defense) | *B. fragilis* | 9E-31 | 96 (88) | Chicken |
| CP1-24 | 549/279 | TACCCGCAACGGGGAGAA CCGATGATACGCTTTCCC AA | 48 | Metabolism (inorganic ion) | *B. fragilis* | 3E-13 | 138 (33) | Chicken |
| CP1-25 | 575/445 | CTGGAGATCATCGTTGAC AGATAGGCTCAAGCAGTA CCGGA | 49 | Information storage and processing | *C. perfringens* str. | 4E-58 | 165 (65) | Chicken and turkey |
| CP1-26 | 544/442 | CCTGTCGTAAAACCCGGG GTCTTCGATTTTCCCTGT TTCA | 50 | Metabolism (carbohydrate) | *B. thetaiotoo-micron* | 3E-37 | 162 (44) | Chicken |
| CP1-40 | 438/244 | TATTTCTGGGTGCGGTTG TACTGACCGGAATGACTC CCA | 51 | General function prediction only | *B. thetaiotoo-micron* | 6E-6 | 114 (30) | Chicken |
| CP1-55 | 391/289 | GTGCGACCGATATGGACC AGAGACATCACCGGAAAC AACA | 52 | Metabolism (amino acid transport) | *B. fragilis* | 2E-17 | 103 (56) | Chicken |

TABLE 2-continued

Description of primers tested for host specificity

| Clone # | Fragment size/PCR product size (DNA bp) | Forward and reverse primer sequences (5'→3') | SEQ ID NO. | COG category | Top BLASTX hit organism (lowest E value) | Expect values | Amino acid Sequence length (%identity) | Primer specificity |
|---|---|---|---|---|---|---|---|---|
| CP1-74 | 493/295 | AGACATCACCGGCAATAA CTACAAGGAGCTATGCCG CTTA | 53 | General function prediction only | B. fragilis | 1E-19 | 115 (43) | Chicken |
| CP2-9 | 251/245 | GTAAGACAGCAACCCCAT GTAACCTATGGTTCAACA CGCTTTA | 54 | Metabolism (inorganic ion) | B. fragilis | 2E-22 | 83 (59) | Chicken |
| CP2-10 | 424/276 | CTTTGCTGCAAGCTCCTT GATACGGAAGCGGAGGAA AG | 55 | Metabolism (nucleotide transport) | B. fragilis | 8E-27 | 91 (61) | Chicken and turkey, geese, and pigeon |
| CP2-17 | 413/377 | CATCTGGGTCATTTGGAT TGAGTTGAAGGCGCAACT GTAAA | 56 | Cellular processes (wall/ membrane) | Lactobacillus acidophilus | 2E-40 | 135 (62) | Chicken, Canadian geese, and pigeon |
| CP2-24 | 456/277 | GACAGTCCTATGGATGCC CAAAAACGGCAGCGCAAA GA | 57 | Information storage and processing | Clostridiaceae | 6E-45 | 111 (98) | Most domestic animals |
| CP2-57 | 514/307 | CGCCTGCGTTCCCTTTAA ATGGGCGCAAGCCTGA | 58 | Cellular processes | B. fragilis | 1E-05 | 106 (31) | Chicken |
| CP2-66 | 487/407 | ATCGGCTACGATTTCCGT TATGTTCGTCGCATGGCT CA | 59 | Cellular processes (defense) | B. fragilis | 4E-19 | 157 (31) | Chicken and turkey |
| CP3-1 | 402/332 | GAACAGGGAGGCGTCTT GAGCGTGCAGGCCCAGA CCCGTA | 60 | Information storage and processing | Bifido- bacterium sp. | 6E-66 | 133 (99) | Most domestic animals |
| CP3-46 | 587/556 | GGAATCACFAGTTTTGGG CGAGCATGGAGGACGATG GTA | 61 | Cellular processes (wall/ membrane) | B. fragilis | 5E-65 | 196 (63) | Chicken |
| CP3-48 | 445/412 | GGCTGCCTGCTCGTCTA CAAGCGGCCTCTTGAGT CCA | 62 | Information storage and processing | C. thermocellum | 6E-45 | 146 (56) | Chicken and turkey |
| CP3-49 | 367/329 | GTCCAGCGCCTCATTGAT TGGTGATCGACTTTTCCA AT | 63 | Metabolism (amino acid transport) | C. tetani | 5E-29 | 122 (53) | Chicken |
| CP3-73 | 395/354 | ACCATTTTGCTTGTCACT GCCAAATGTAAGCCGCAA AGATGA | 64 | Cellular processes (wall/ membrane) | L. gasseri | 1E-19 | 131 (38) | Chicken and other birds |

Generally, there were no major differences in COG categories between CP and CB libraries, although cellular processes associated with cell motility and metabolic functions associated with lipid transport were present only in the CP library, while metabolic functions associated with nucleotide transport were present only in the CB library, as shown in FIG. 7. These results suggests that regardless of the type of blocking DNA used, it is possible to obtain similar COG subcategories of genes specific to the chicken microbial community by using the GFE approach. As stated above, the same gene was represented several times within a library (e.g., dine CB-R2-27) and shared between the different libraries (e.g., clone CP 2-10, as shown in Table 2). Considering the complexity of the metagenomes and the limited number of clones analyzed herein, the probability of randomly enriching for the same gene in independent libraries is significantly low. Consequently, these results provide further evidence of the effectiveness of GFE as an approach to select for genes that are unique to the microbial community under study.

Development of Host-Specific Primers

Twenty fine sequences were selected from the clone libraries to develop host-specific PCR assays based on the following criteria:

1. showed similarity to *Clostridia*, *Bacteroidetes* and *Lactobacillus* like proteins;

2. showed similarity of characterized proteins involved in information storage, cellular process and metabolism, and
3. showed similarity to membrane-associated proteins.

To test host specificity, the PCR assays were challenged against composite fecal DNA extracts form non-target animals and from the chicken composite sample used in the GFE experiments. All primers tested discriminated between testers and blockers (pig in CP and turkey/goose/seagull in CB, respectively). Of the CP-based assays, ten were shown to be chicken specific, three produced amplification products for both chicken and turkey fecal DNA, four assays were positive with fecal DNA from all birds tested (chicken, turkey, seagull and goose), and two cross-reacted with non-avian hosts, as shown in Table 2.

Two assays from the CB sequences were specific to chicken fecal DNA, while the rest also cross-reacted with sheep and/or goat fecal DNA. Of the ten PCR assays targeting cellular related processes, eight of them were shown to be chicken or bird specific. These results are compatible with previous studies showing that functional gene sequences associated with cellular processes are good targets for host-specific PCR assays.

Of the seven DNA sequences possibly related to metabolism, five of these sequences were specific to chicken fecal bacteria (Table 2). Those five DNA sequences were similar to cell membrane proteins involved in the transport of carbohydrates (e.g., CP1-26), inorganic ions (e.g., CP1-24 and CP2-9), amino acids (e.g., CP1-55 and CP3-49), and nucleotides (CP2-10). Sequences related to proteins involved in information storage/processing and pooling characterized functions (CP1-25, CP3-48, CB-R2-42. CP1-40 and CP1-74) were specific to a narrow range of hosts (i.e., chicken and/or turkey). Therefore, these results suggest that host-specific sequences can be found in several COG categories.

Several enriched gene fragments have phylogenic relevance, such as CP1-25, which is similar to the elongation factor G of *Clostridium* spp. The latter gene is a homolog of elongation factor Tu, a GTP-binding protein that plays a central role in protein synthesis and that has been used as a phylogenetic marker. This is the first phylogenetic gene in addition to the rRNA gene to be potentially useful for developing host-specific markers.

Sequences similar to *Bacteroidetes* proteins used for PCR assays showed mainly chicken-specific or chicken/turkey-specific signals, while the *Clostridia*- and *Lactobacillus*-based PCR assays generated positive signals with fecal DNA of other birds as well. *Bacteroidetes* 16S rDNA-based methods have been previously shown to discriminate between human and cattle fecal microbial communities; however, 16S rDNA sequences gave not been useful in development of chicken-specific assays.

The present inventors have demonstrated that non-ribosomal *Bacteroidetes*-like genes were identified as specific to chicken and avian microbial communities using a metagenomic approach. These results are not surprising, as several studies have shown that *Bacteroidetes* spp. have developed a host-specific relationship with their host. For example, *Bacteroidetes* spp. are beneficial to the human immune system and human metabolism and can also obtain specific nutritional benefits fro the host gut cells in the form of a diversity of available glycans. Genomic and proteomic data gave provided relevant insights into the nature of the interactions between this commensal bacterial group and the human and mouse gut.

It appears from the studies reported herein that some *Bacteroidetes*-like populations might also develop host-specific interactions with non-mammalian host types. It also appears that *Clostridia*- and Bacilli-like proteins might be involved in broad symbiotic interacts, as evidenced by the presence of similar host-specified genetic markers in different avian species.

The geographic distribution of all twelve chicken-specific assays was determined by first challenging each assay against fecal DNA composites of chickens from Delaware, West Virginia, Ohio and Georgia. Differences in the geographic distribution of host-specific markers were observed for most of the PCR assays, as shown in Table 3. For example, all PCR assays produced a positive signal with WV composite chicken fecal samples. It should be noted, however, that WV chicken fecal DNA extracts were used as the tester pool in the GFE experiments. In contrast thereto, several PCR assays did not amplify 'DNA from fecal samples collected at other sample areas (e.g., CP1-74, CP1-40 and CP3-46). The host distribution of PCR assays that produced positive signals with two or more of the chicken composite fecal DNA templates were challenged against 40 individual chicken feces from the aforementioned geographic locations and 30 individual chicken feces collected in China. Different levels of host distribution were obtained for each of the assays, as shown in Table 3. Three of the PCR assays (CP2-9, CP3-49 and CB-R2-42) amplified at least a third of the individual fecal samples. Nearly half of the chicken samples from China tested positive with three assays, suggesting that these markers are globally distributed and that these PCR assays may be useful for water monitoring in other countries. The PCR assays developed this far were generated by examining a small fraction of the cloned fragments. It is reasonable to expect that the pool of host-specific assays will increase as the number of clones examined increases. The results obtained here indicate that metagenomic enrichments allow for the rapid development of multiple genetic markers to confirm the presence of chicken (or other animal) fecal pollution in waters.

TABLE 3

Estimated host distribution of chicken-specific PCR assays

| Animal type | Sampling locations | Number of fecal samples | CP2-9[a] | CP3-49 | CB-R2-42 | CP1-74 | CB-R2-80 | CP3-46 | CP1-40 |
|---|---|---|---|---|---|---|---|---|---|
| Chicken | DE, US | 12 | 0 | 1 | 1 | 1 | 0 | 1 | 1 |
| Chicken | WV, US | 15 | 3 | 3 | 2 | 2 | 5 | 3 | 2 |
| Chicken | OH, US | 9 | 8 | 6 | 5 | 8 | 5 | 2 | 1 |
| Chicken | GA, US | 4 | 3 | 2 | 1 | 2 | 1 | 1 | 0 |
| Chicken | Shandong, China | 30 | 14 | 13 | 15 | 2 | 0 | 2 | 0 |
| No. of positive signals[b] | — | 70 | 28 (40%) | 25 (36%) | 24 (34%) | 15 (21%) | 11 (16%) | 9 (13%) | 4 (6%) |

TABLE 3-continued

Estimated host distribution of chicken-specific PCR assays

| Animal type | Sampling locations | Number of fecal samples | CP2-9[a] | CP3-49 | CB-R2-42 | CP1-74 | CB-R2-80 | CP3-46 | CP1-40 |
|---|---|---|---|---|---|---|---|---|---|

[a]Refers to specific PCR assay.
[b]Percentage is the number of positive signals to total fecal samples tested in a certain location.

The detection limit of the CP2-9, CP3-49 and CB-R2-42 assays was determined using fecal DNA extracts from three different locations: West Virginia, Ohio and China. The results show different levels of sensitivity for each of the assays, ranging from 0.001 to 1 ng/microliter of fecal DNA, as shown in Table 4, with the CP2-9-based assay consistently having the highest detection limit. Each assay showed different levels of detection of different fecal samples, suggesting that the density of the population carrying the host-specific markers can vary even among individual hosts, as shown in Table 4. In most cases, the sensitivity of the host-specific assays was lower than assays targeting *Bacteroidetes* and *Clostridia*-like sequences (Table 4), suggesting that the markers are found in a subset of the most predominant fecal bacteria, a phenomenon also observed with 16S rDNA-based markers.

Laboratory Application of Genome Fragment Enrichment

Initially, 70 cow-specific DNA sequences isolated from cow fecal material were identified using the GFE method of the present invention. Three of these sequences were randomly chosen to develop cow discriminatory primer sets, and full scale working applications.

Three randomly selected host-specific *Bacteroidales*-like GFE sequences were used for host-specific PCR primer development (Table 1). PCR assay 1 was derived from a 368 bp host-specific DNA fragment annotated as a conserved hypothetic secretory protein with an unclassified functional group assignment (locus BT0921). The top BLASTx hit ($8.00E^{-11}$) for this sequence shared 25% sequence identity to a *B. fragils* YCH46 hypothetical protein (locus BF2432).

TABLE 4

PCR assay detection sensitivity (ngDNAµl$^{-1}$) of chicken fecal DNA and environmental sample DNA possibly polluted by chicken manure

| Sample | Source (DNA extract) | CP2-9 | Cp3-49 | CB-R2-42 | *Clostridia*[a] | *Bacteroidetes*[a] |
|---|---|---|---|---|---|---|
| WV8 | Chicken feces | 1 | 1 | 0.01 | 1 | 1 |
| WV9 | Chicken feces | 1 | 1 | 0.1 | 0.0001 | 1 |
| WV11 | Chicken feces | 1 | 0.01 | 0.01 | 1 | 1 |
| WV12 | Chicken feces | 0.1 | 1 | 0.01 | 0.0001 | 0.01 |
| OH4 | Chicken feces | 0.01 | 1 | 1 | 0.01 | 0.01 |
| OH5 | Chicken feces | 1 | 1 | 0.1 | 0.01 | 1 |
| OH6 | Chicken feces | 0.1 | 0.01 | 1 | 0.01 | 0.01 |
| OH10 | Chicken feces | 0.1 | 1 | 0.1 | 0.01 | 0.01 |
| China1 | Chicken feces | 0.1 | 0.01 | 0.01 | 0.001 | 0.001 |
| China3 | Chicken feces | 0.01 | 1 | 0.1 | 0.0001 | 0.0001 |
| China10 | Chicken feces | 0.01 | 0.001 | 0.001 | 0.0001 | 0.001 |
| China13 | Chicken feces | 0.01 | 0.001 | 0.001 | 0.0001 | 0.0001 |
| DH2, GA | Water filtrate sample | 0.1 | — | — | 0.001 | 0.001 |
| DH4, GA | Water filtrate sample | 1.0 | — | — | 0.01 | 0.01 |
| Whitleyburg, DE | Water filtrate sample | — | 0.1 | 0.1 | 0.01 | 0.01 |
| Brownsville, DE | Water filtrate sample | — | 0.1 | 1 | 0.01 | 0.01 |

[a]General PCR assays targeting members of *C. coccoides* and *Bacteroidetes* species.

When the three best PCR assays (CP2-9, CP3-49 and CB-R2-42, based on the host distribution results) were challenged against water samples presumed to be contaminated with non-target sources (i.e., cattle, human, pigs, and geese), none of the DNA extracts produced PCR signals, further suggesting the host specificity of these markers. In contrast, when DNA extracts from water samples obtained from Georgia and Delaware watersheds possibly contaminated with chicken feces (see Table 5, Figure *) were used as templates, the CP2-9 assay showed positive signals in one Delaware and two Georgia samples, while the other two assays detected chicken-associated signals in two of the Delaware DNA extracts. None of the markers detected chicken contamination in two Delaware samples. In water samples, the minimal detection limit was 0/1 ng. These results suggest that it may be necessary to use multiple markers when trying to detect any particular source of fecal contamination. Before using any assay in fecal source tracking studies, extensive field testing is required to determine the efficacy of the assays and the geographic distribution of the host-specific markers.

Under optimal PCR conditions (62° C. annealing 30 cycles), PCR assay 1 routinely detected fg quantities of cow fecal DNA (FIG. 4A).

PCR assay 2 targeted a portion of 437 bp fragment annotated as a HDIG domain protein involved in energy metabolism and electron transport (locus BT2749). The top BLASTx hit for PCR assay 2 (32% ID; $1.00E^{-08}$) was a *B. fragils* YCH46 putative membrane-associated HD superfamily hydrolase. Optimal conditions for PCR assay 2 include a 62° C. annealing temperature for 35 cycles, which allowed for the detection of 10 fg cow fecal DNA, as showing FIG. 4B.

PCR assay 3 originated from a 569 bp fragment encoding for a sialic acid-specific 9-O-acetylesterase secretory protein homologue (locus BT0457) functioning cell envelope biosynthesis and degradation of surface polysaccharides and lipopolysaccharides. The top BLASTx hit for marker 3 (75% ID; $8.00E^{-80}$) was a sialate O-acetylesterase protein from *B. fraglis* YCH46. PCR assay 3 exhibited the lowest limit of detection under optimal conditions (60° C.; 35 cycles) and consistently amplified 0.1 fg of cow fecal DNA (FIG. 4C). In addition, three novel PCR assays and two real-time PCR tests specific for cattle fecal microbes have also been developed and are listed in Table 1.

All host-specific markers amplified template DNA molecules from the original target GFE cow fecal sample, as well as from a large number of individual cow fecal samples not used to construct host-specific GFE clone libraries. Host-specific markers were present in 72% to 91% of 148 cow fecal samples collected from five different geographical locations over a 24-month period (Table 4). PCR assay 3 showed the broadest host distribution and temporal stability by successfully amplifying 91% of all cow fecal samples.

Each primer set was tested against individual non-target DNA molecules. PCR assay 3 exhibited specificity for 99.2% of the fecal samples and only cross-reacted with two alpaca samples. Primer sets demonstrated extremely high levels of specificity in fresh and marine natural water sources. All water samples yielded no PCR product suggesting that indigenous microorganisms from these water sources do not cross-react with host-specified target DNA sequences.

Table 5 provides a summary of host-specific PCR primer sequences, amplicon lengths in base pairs, optimal annealing temperatures (° C.), optimal number of PCR thermal cycles, and limit of detection.

TABLE 5

Optimal reaction conditions, limited of detection and primer sequences of host-specific PCR assays.

| Primer Set | Sequence (5' to 3') | SEQ ID NO. | Amplicon Length (bp) | Optimal Annealing Temp (° C.) | Optimal Cycle No. | Limit of Detection |
|---|---|---|---|---|---|---|
| Bac1F | TGCAATGTATCAGCCTCTTC | | | | | |
| Bac1R | AGGGCAAACTCACGACAG | 1 | 196 bp | 62° C. | 30 | 1 fg |
| Bac2F | ACAAGCCAGGTGATACAGAAAGa | | | | | |
| Bac2R | GCTTGTTGCGTTCCTTGAGATAAT | 2 | 274 bp | 62° C. | 35 | 10 fg |
| Bac3F | CTAATGGAAAATGGATGGTATCT | | | | | |
| Bac3R | GCCGCCCAGCTCAAATAG | 3 | 166 bp | 60° C. | 35 | 1 ag |
| Bac4F | TGGGAATGGCGGTAATCTCG | | | | | |
| Bac4R | CAACAGCCGGTCGTCTTCCT | 4 | 187 bp | 65° C. | 35 | — |
| Bac6F | ACTCCCTGCGCTCCGAAGATA | | | | | |
| Bac6R | GGCCCAGGCACCATTTACAGT | 5 | 150 bp | 65° C. | 35 | — |
| Bac8F | CTCCGTCTTTCTCCGTCCTGTTCT | | | | | |
| Bac9R | GATCCCCCTCGCCTCCGTCCT | 6 | 430 bp | 65° C. | 35 | — |
| Hum76Fa | TAAAGGTCCCGGAGAAGGTAT | | | | | |
| Hum76Ra | AATCCGGATGCGTTTTTAGA | 7 | 209 bp | 58° C. | 35 | — |
| Hum163Fa | CGTCAGGTTTGTTTCGGTATTG | | | | | |
| Hum163Ra | AAGGTGAAGGTCTGGCTGATGTAA | 9 | 165 bp | 60° C. | 35 | — |
| Hum181Fb | GTAATTCGCGTTCTTCCTCACAT | | | | | |
| Hum181Rb | ACCTGCAAACCGTACAAGAAAAA | 11 | 110 bp | 61° C. | 35 | — |
| Hum336Fa | CCAACGGCGTAACTTCTTCA | | | | | |
| Hum336Ra | ATTACCGGATTACAAACCTTATG | 12 | 162 bp | 62° C. | 35 | — |
| CP6F | TATTTCTGGGTGCGGTTGTA | | | | | |
| CP6R | CTGACCGGAATGACTCCCA | 13 | 244 bp | 64° C. | 35 | 0.4 pg |
| CP4F | CTGGAGATCATCGTTGACAGA | | | | | |
| CP4R | TAGGCTCAAGCAGTACCGGA | 14 | 445 bp | 65° C. | 35 | 40 pg |
| CB6F | CGTGAATTTCCGCTACGA | | | | | |
| CB6R | CCTCTTCCTTGCGTCCCA | 15 | 287 bp | 64° C. | 35 | 4 pg |
| cowM2F | CGGCCAAATACTCCTGATCGT | | | | | |
| cowM2R | GCTTGTTGCGTTCCTTGAGATAAT | 16 | 92 bp | 60° C. | 40 | — |

TABLE 5-continued

Optimal reaction conditions, limited of detection and primer sequences of host-specific PCR assays.

| Primer Set | Sequence (5' to 3') | SEQ ID NO. | Amplicon Length (bp) | Optimal Annealing Temp (° C.) | Optimal Cycle No. | Limit of Detection |
|---|---|---|---|---|---|---|
| cowM3F | CCTCTAATGGAAAATGGATGGTATCT | | | | | |
| cowM3R | CCATACTTCGCCTGCTAATACCTT | 17 | 122 bp | 60° C. | 40 | — |
| M2probe | [DFAM]AGGCACCTATGTCCTTTA CCTCATCAACTACAGACA[DTAM] | 18 | | | | |
| M3probe | [DFAM]TTATGCATTGAGCATCGA GGCC[DTAM] | 19 | | | | |

In validation studies, all three cow-specific PCR assays were found to differentiate between cows and 29 other animal species and did not amplify DNA isolated from freshwater and marine microbial communities. These assays also successfully identified cow fecal pollution from water samples collected in two watersheds situated near cow animal feeding operations. Based upon the fact that three randomly chosen sequences worked according to plan, one skilled in the art would expect that the remaining 67 sequences would work just as well. It is also reasonable to expect that human and chicken-specific DNA sequences isolated during GFE will allow for the development of additional human- and chicken-specific PCR assays.

Genome fragment enrichment has been successfully used to identify hundreds of DNA sequences either absent or divergent in one bacterial genome compared to another, as well as microbial cow-, human-, and chicken-specific DNA sequences.

GFE Technical Protocol

A. Biotin Labeled "Capture Fragment" Preparation

While the protocol described below uses microgram quantities of DNA, GFE has been successfully performed with much smaller starting quantities of DNA. The key to using much smaller quantities of DNA is to maintain specific ratios between target, blocker, and capture surface. It is crucial to use large quantities of blocker DNA relative to the capturing surface for the prehybridization step. In some of the examples in the present specification, approximately 50 times more blocker was used than capturing surface DNA, and one-tenth the amount of capturing surface DNA for target DNA. A lower limit is approximately 1:2 and 1:1 ratios of capture: target. Ideally, one creates a competitive hybridization environment in which the blocked DNA has the advantage, both in quantity of DNA and time, to hybridize to complementary DNA sequences in the capturing surface. This advantage is realized in the prehybridization step, where competitive hybridization of the capturing surface of the capturing surface, the blocking DNA, physically blocks DNA sequences shared between two DNA pools. The unblocked DNA hybridization sites remaining after prehybridization are then available to form DNA hybrids with the terminal tagged target DNA, which is at a disadvantage to the blocker DNA both in quantity of DNA and time to hybridize.

For the comparison of two microbial genomes, E. faecalis genomic DNA 1.8 µg was mechanically sheared by sonication into approximately 150 to 900 base pair (bp) fragments, precipitated in 7.5 M ammonium acetate and 100% ethanol, and dissolved in 15 µg TE (1.0 mM Tris, 0.1 mM EDTA, pH 7.5). DNA was mixed with 1.8 µg of photoactive biotin (PBA; Sigma) and transferred to three 0.2 ml thin wall PCR microtubes in equal volumes to increase the surface area of direct exposure to the light source. Each microtube was placed on ice under a regular 200-watt incandescent light bulb, distance 5 cm, for 20 minutes. The three aliquots were then combined, diluted tenfold with TE (pH 9.0), and extracted with three volumes of n-butanol to remove unincorporated PAB. The supernatant was then discarded, and the remaining solution was split into three equal volumes and concentrated by ammonium acetate and ethanol precipitation.

B. Blocking DNA Preparation

Blocking DNA can be prepared in any number of ways familiar to one skilled in the art. In the present example, sheared native DNA was used rather than PCR amplified DNA in order to reduce amplification bias in the blocker DNA fragment pool.

To prepare blocking DNA for pre-hybridizing capture fragments as shown in FIG. 1, 30 µg of E. faecium genomic DNA were sheared, divided into three equal volumes, precipitated with 7.5 M ammonium acetate and 100% ethanol, and dissolved in 30 µl TE (10 mM Tris, 0.1 mM EDTA, pH 7.5)

C. Target DNA Preparation

Four micrograms of E. faecalis genomic DNA were sheared by sonication, precipitated in 7.5 M ammonium acetate and 100% ethanol, and dissolved in 5 µl TE (pH 7.5). Defined terminal sequences were added to these capture target fragments to allow PCR amplification of sequences enriched by competitive hybridization. DNA fragments were re-suspended and incubated at 95° C. for five minutes with 4.5 µg K9-DNA primer (5'GACACTCTCGAGACATCACCGG-TACC-NNNNNNNNN-3') SEQ ID NO:33. This primer illustrates one of many primers that can be used. The most important characteristics of a primer for use in the present invention are that the sequence works well for T-PCR and to have a random polymer 3' sequence. The mixture was then cooled on ice for five minutes and primers extended with 50 units DNA polymerase I Klenow fragment as described by the manufacturer (New England BioLabs) for 3.5 hours. Klenow extension products containing tagged termini were purified using a QiaQuick PCR Product Clean-up Kit (Qiagen).

A single primer amplification step was then performed to initially amplify K9-targeted DNA. This has previously been shown to produce a reasonable representation of the original material with DNA fragments of this size. Reactions (100 µl) contained 1× ExTaq PCR buffer (Invitrogen); 2.5 mM each dATP, dCTP, dGTP, and dTTP; 0.2 µM of K9-PCR primer (5'-GACACTCTCGAGACATCACCGG-3') SEQ ID NO:34; to acetamide; 0.625 U ExTaq, and 10 ng of tagged DNA. Incubation temperatures were 94° C. for 40 seconds, 53° C. for one minute, and 72° C. for 30 seconds, for 28 cycles, followed by a 72° C. extension step lasting 1.5 minutes. PCR products were purified using a QiaQuick PCR Product Cleanup Kit (Qiagen).

A single primer amplification step was then performed to initially amplify K9-tagged target DNA. This has previously been shown to produce a reasonable representation of the original material with DNA fragments of this size (Tarr et al., *Journal of Bacteriology* 182: 6183-6191, 2000). Reactions of 100 µl each contained 1× ExTaq PCR buffer (Invitrogen), 2.5 mM (each) of dATP, dCTP, dGTP and dTTP, 0.2 µM of K9-PCR primer (5'-GACACTCTCCGAGACATCACCGG-3') SEQ ID NO:35, 1% acetamide, 0.625 U Ex Taq, and 10 ng of tagged DNA. As noted above, a different primer can be used, depending upon the terminal sequence used to tag the target DNA. Incubation temperatures were 94° C. for four seconds, 53° C. for one minute, and 72° C. for 30 seconds for 28 cycles followed by a 72° C. extension step for 1.5 minutes. PCR products were purified using a QiaQuick PCR Product Clean-up Kit (Qiagen). All PCR reactions in this study were performed in either low-retention reaction tubes (0.2 ml) or 96-well polypropylene plates using a MJ Research DNA Engine Tetrad 2 thermal cycle.

The temperatures for hybridization used in GFE depend on the physical properties of the DNA used as target, blocker, and capturing surface. Hybridization temperatures from about 40° C. to about 70° C. have successfully been used in GFE.

D. Prehybridization and Capture Hybridization

Two independent full analyses were performed. For each enrichment, 10 µg of blocking *E. faecium* DNA and 0.6 µg of biotinylated *E. faecalis* capture DNA were precipitated in ethanol, resuspended in 20 µl EPPS solution (10 mM EPPS, 1 mM EDTA), overlaid with mineral oil, and incubated at 98° C. for two minutes. The incubation temperature was then reduced to 55° C., 4 µl of 5M NaCl were added immediately, and the solution was allowed to self-hybridize for 30 minutes. Five micrograms of K9-tagged *E. faecalis* PCR product was resuspended in 20 µl of EPPS solution and incubated at 98° C. for two minutes in a second microtube. These two solutions were then mixed together and incubated at 55° C.

E. Capture of Target-Specific DNA

Biotinylated DNA hybrids were isolated from the hybridization mixture with Dynabeads M-280 Streptavidin (Dynal Biotech, Brown Deer, Wis.). First, 60 µl of beads were washed with 100 µl B & W buffer (TE, pH 7.5, 2M NaCl) three times. Biotin labeled DBNA was immobilized to the bead surface by mixing washed beads and the hybridization reaction diluted in 500 µl if water at 42° C. for ten minutes. The beads were separated from the diluted hybridization mix with a magnetic particle concentrator (MPC-S; Dynal Biotech (and washed three times with 100 µl SG1 Buffer (0.5 M NaOH, 0.1 M NaCl) and incubated for ten minutes at 37° C. The resulting eluate was then precipitated in ammonium acetate and ethanol and resuspended in 80 µl TE (pH 7.5). Eluted K9-tagged target *E. faecalis* DNA molecules were selectively amplified as previously described above. The PCR products were purified, pooled, and used as target DNA for a second round of prehybridization and hybridization. The PCR products from the second round were used for a third round.

Initially, it was believed that three rounds of GFE were necessary to isolate unique DNA fragments. However, it has been found that one enrichment round is sufficient.

DNA Sequencing

PCR products from the third round of each independent GFE were incorporated into pCR4.1 TOPO as described by the manufacturer, Invitrogen. Individual clones were then subcultured in 300 µl of Luria Broth containing 10 µg/ml ampicillin, and corresponding plasmid purified prior to screening by PCR for inserts. PCR reactions (25 µl) contained 1× ExTaq PCR buffer (Invitrogen), 2.5 mM (each) dAPT, dCTP, dGTP, and dTTP, 0.2 µM of M13F (5'-GTAAAAC-GACGGCCAG-3') SEQ ID NO:36 and M13R (5'-CAG-GAAACAGCTATGCA-3') SEQ ID NO:37 primers, 0.064% bovine serum albumin (Sigma), 0.625 U ExTaq and 1 µl of template. Incubation temperatures included 94° C. for three minutes lysis step followed by 20 cycle of 94° C. for 30 seconds, 52° C. for 20 seconds, and 72° C. for 40 seconds. Prior to sequencing, PCR products were purified using Qiaquick 96 Plate (Qiagen). Screening was performed in both directions at the Cincinnati Children's Hospital Medical Center Genomics Core Facility (Cincinnati, Ohio) by the dye-terminator method using an Applied Biosystems PRISM 3730 DNA Analyzer.

Dot Blot Hybridizations

To confirm genetic variation in the *E. faecalis* chromosomal regions identified, dot blot hybridizations were performed with the cloned regions using *E. faecium* DNA as a probe (Ausubel et al., 2001). PCR products for each enriched DNA sequence were purified using the QiaQuick PCR Purification Kit (Qiagen) and 10 µl of PCR product were denatured with 45 µl of denaturing solution (0.5 M NaOH, 1.5 M NaCl) prior to spotting directly onto nylon membranes (Licor) using a 96-2311 manifold (BioRad). The membranes were neutralized with 10 µl neutralization solution (1M TrisCl pH 8.0, 1.5 M NaCl), and UV cross-linked using a Stratalinker (Stragene) following the manufacturer's instructions. Prehybridization was performed for 1.5 hours at 65° C. in 9 ml of pre-warmed Odyssey DNA Hybridization solution (Licor) containing 1×Denhardt's solution (Sigma) and salmon sperm DNA (Sigma). For probe synthesis, defined terminal sequences were added to *E. faecium* genomic DNA as described above [GFE (iii) using F9-DNA 5'-GCCG-GAGCTCTGCAGAATTC-NNNNNNNNN-3']. F9-tagged DNA was amplified as described above [GFE (iii) using biotin-16-2'deoxyuridine-5'-triphosphate (Roche) and the F9-PCR primer [5'-GCCGGAGCTCTGCASGAATTC-3']. The F9-tagged biotin labeled *E. faecium* PCR product was purified using QiaQuick PCR Purification Kit (Qiagen). Approximately one microgram of probe (20 µl of PCR product) was added to fresh hybridization solution and allowed to hybridize spotted membranes overnight at 55° C. in a rotating hybridization oven. Standard protocols for membrane washing were followed, washing twice under low stringency conditions (room temperature) and twice under moderate stringency conditions (42° C.) (Ausubel et al., 2001). The membranes were visualized with ah Odyssey infrared imaging system (Licor) at an intensity setting of five.

Data Analysis

DNA sequence readings were assembled using SeqMan II (DNAstar, Inc.) and compared to the *E. faecalis* V583 annotated genome at The Institute for Genomic Research (TIGR) with BLASTn. Redundant sequences were removed from the data set. The remaining sequences were then searched against the *E. faecium* genome draft assembly using the JGI tBLASTx (Joint Genome Institute). The sequences were designated homologous (expectation value $\leq 1e^{-03}$) or absent (no significant hits). Gene attributes were assigned to specific clones based on annotations available at the TIGR comprehensive microbial resource database.

DNA sequence identities between *E. faecalis* (ATCC #19433) and *E. faecalis* V583 were calculated using BLASTn (Althschul et al., 1997) generated alignments. Sequence identities between *E. faecalis* (ATCC #19433) and the *E. faecium* draft assembly (JGI) were derived from pair wise DNA sequence comparisons using the Wilbur-Lipman method with default settings (MegAlign, DNAstar, Inc.).

Non-redundant clones, false positives, and divergent clones were categorized with cross-species alignments using the JGI BLATn and the *E. faecium* genome draft assembly database. BLATn was performed with default settings and minimum sequence identity settings of 90% and 80%. Sequences were sorted into two groups using the following criteria:
- A. Sequences that share a ≧90% sequence identity with an *E. faecium* homologue were labeled false positives, and
- B. sequences that did not have a match with ah 80% minimum identity were placed in the divergent clones category.

Results

Summary of *E. faecalis* GFE Clones

GFE was performed with chromosomal DNA from two enterococcal ATCC type strains. Three hundred total *E. faecalis* DNA fragments between 163 and 853 base pairs in size were obtained as plasmid inserts following three rounds of GFE in two independent experiments. Analyses of these DNA fragments identified 225 non-redundant sequences (Table 2, GenBank accession numbers CZ191135-CZ191359). Several of these sequences, of 13.7% (n=31) corresponded to variable regions within ribosomal operons, including 16S, 23S and intercistronic spacer regions (ISR) DNA sequences. There are four such operons in the *E. faecalis* V583 genome (Paulsen et al., 2003). This large number of ribosomal clone sequences may have resulted from PCR kinetics that preferentially amplified the more abundant nucleic acid templates. These non-redundant clones from *E. faecalis* shared an average of 97.8% sequence with *E. faecalis* V583, indicating numerous strain-dependent polymorphisms, and only an average of 36% sequence identity with *E. faecium* (JGI) sequences, as shown in Table 6. The average identify of the enriched clone set to *E. faecium* was considerably lower than a set of randomly selected *E. faecalis* V583 genome regions, which showed an average of 58% identity to *E. faecium* (JGI) draft sequences. Thirty two percent (n=71) of all *E. faecalis* non-redundant GFE clone sequences were entirely absent from the *E. faecium* genome draft assembly (JGI).

GFE Sequence Characterization

As expected, BLASTn searches against the NCBI GenBank database identified homologous *E. faecalis* V583 sequences for all 224 non-redundant sequenced clones (Galbraith et al., 2004; Nesbo et al., 2002) (Expectation value cut-off of $\leq 1\times 10^{-6}$). Only 154 homologous sequences in the *E. faecium* JGI genome draft assembly could be identified using BLASTp and tBLASTx using an expectation value cut-off of $\leq 1\times 10^{-3}$). These *E. faecalis*-specific clone sequences were sorted into nine functional groups based on the annotated complete genome sequence of *E. faecalis* V583.

The groups consisted of the following:
1. phage open reading frames;
2. putative stress response proteins;
3. sugar or polyol utilization pathway proteins;
4. transport and binding proteins;
5. ribosomal sequences;
6. fragments containing untranslated regions;
7. hypothetical or conserved domain proteins;
8. putative surface-exposed or membrane associated proteins; and
9. others.

GFE clone groupings were based on predicted attributes. The percentages of clones conserved across all sequences low-GC Gram-positive bacteria (excluding mycoplasmas, FASTA p-value<$10^{-5}$) are listed in Table 3. The most frequently assigned gene functional group for all non-redundant GFE clones was the *E. Faecalis* V583 genome annotated putative surface exposed or membrane associated proteins (22.6%) (Table 7). The percentage of GFE clone sequences conserved across all known low-GC Gram-positive bacteria was only 27.2% for those sequence with an *E. faecium* homologue, and only 5.6% for clone sequences absent in the *E. faecium* genome draft assembly (Table 7).

TABLE 6

Summary of sequenced DNA clones obtained by three rounds of GFE

| *E. faecalis* GFE Clone Classification | No. of clones | Average Length (bp) | % Sequence ID to *E. faecalis* | % Sequence ID to *E. faecium* |
|---|---|---|---|---|
| All non-reduced clones | 225 | 401 | 97.8% | 36% |
| Homolog present in *E. faecium* | 154 | 410 | 98% | 64.5% |
| No homolog present in *E. faecium* | 71 | 380 | 96.8% | 0% |
| False positive clones (≧90% ID to *E. faecium* homolog) | 32 | 424 | 99% | 95% |
| Divergent clones (≦80% ID to *E. faecium* homolog) | 184 | 399 | 97.6% | 34.4% |

TABLE 3

Functional group assignment of non-redundant GFE clones and percent and conserved among all sequenced low-GC Gram-positive bacteria[a]

| E. faecalis GFE Clone Classification | No. | Sur | UTR | Rib | Hyp | Tran | Path | Str | Ph | % Con |
|---|---|---|---|---|---|---|---|---|---|---|
| All non-reduced clones | 225 | 51 | 34 | 31 | 23 | 27 | 18 | 15 | 10 | 20.4% |
| Homolog present in E. faecium | 154 | 32 | 26 | 31 | 7 | 20 | 15 | 13 | 4 | 27.2% |
| No homolog present in E. faecium | 71 | 19 | 8 | 0 | 16 | 7 | 3 | 2 | 6 | 5.6% |
| False positive clones (≧90% ID to E. faecium homolog) | 32 | 1 | 0 | 31 | 0 | 0 | 0 | 0 | 0 | 100% |
| Divergent clones (≦80% ID to E. faecium homolog) | 184 | 50 | 31 | 0 | 23 | 26 | 17 | 13 | 10 | 22.8% |

Thirty four E. faecalis-specific DNA regions were identified by GFE (Table 7) using a more stringent criterion of at least two corresponding GFE clones. For example, five non-redundant GFE clones corresponded to a region predicted to encode for a 5'-nucleotidase family protein and adjacent putative pheromone binding protein (E. faecalis V583, segment 1; region 64,598 to 66,703). Fourteen divergent gene regions potentially encode for proteins annotated as surface exposed or membrane associated open reading frames (Paulsen et al., 2003). In the two independent GFE hybridizations, 76.5% of these 34 DNA regions were identified in both experiments (Table 7), demonstrating good consistency for the method.

Identification of False Positives and Divergent Clones

Cross-species alignments with JGI BLATn identified 32 false positive final GFE clones (≧90% identity with an E. faecium homologue) and 184 significantly divergent clone regions (≦80% identity with an E. faecium homologue). These 90% and 80% cut-offs were selected based on data from previous genome studies. rDNA clone sequences made up all of these false positives (97%) except for a cell wall surface anchor family protein (locus EFI1896, coordinates 6208-6525). The sequence identity of this cell wall surface anchor family protein was only 89%, but it remained a significant hit with the E. faecium JGI BLATn search because of a 40 bp stretch contained a 90% or greater DNA sequence identity.

Figure 4:
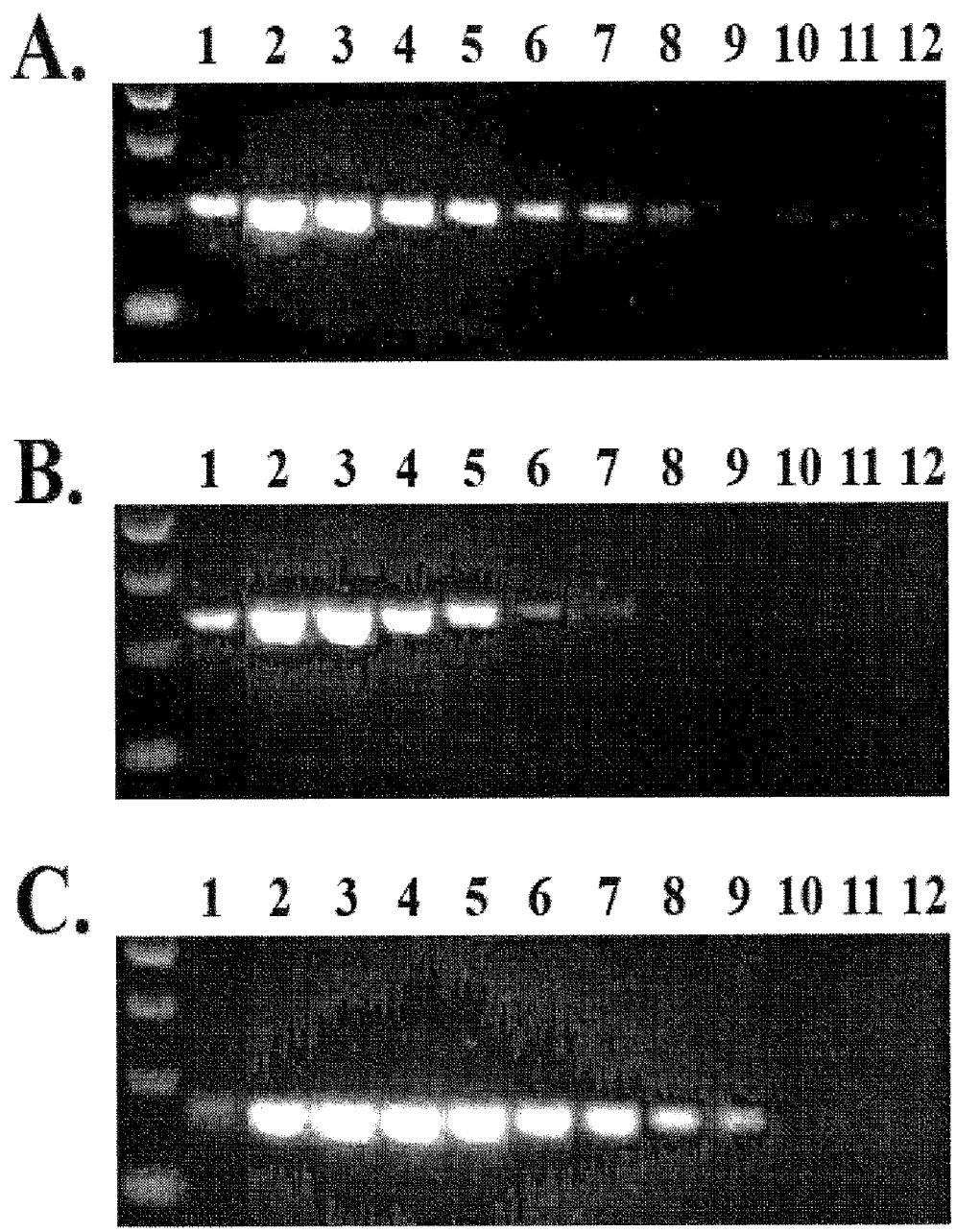

Dot blots using E. faecium genomic DNA as a probe identified 62 cross-hybridizing false positive DNA sequences (FIG. 4). These clone inserts exhibited an average of a 69% sequence identity to E. faecium homologous sequences. Dot blot analysis correctly recognized 31 of 32 (97%) of the false positives calculated from the BLATn false positive screen, demonstrating a high level of agreement between the bioinformatics and experimental false positive screens.

Of the 71 clone sequences completely absent in E. faecium (Table 6), only 7 elicited positive results with the dot blot assay (9.8%). These sequences may have very short regions capable of probe hybridization. These results provide experimental confirmation that numerous regions of genetic variation have been identified for these two specific ATCC strains, and are in good agreement with bioinformatic analyses based on the two sequenced strains. Over 90% of GFE sequences absent from the E. faecium genome draft (JGI) also showed no hybridization in the analyses conducted. Dot-blot hybridization also provides a valuable secondary screening method to identify directly GFE false positives when bioinformatic information is not available.

Identification of E. faecalis DNA Sequences Absent or Divergent in E. faecium

Several hundred candidate E. faecalis-specific DNA sequences were obtained by GFE, and specificity was confirmed for a subset of these genomic regions confirmed by dot blot hybridization and a comparative bioinformatic analysis. GFE clones (excluding false positives identified by BLATn) exhibited an average of only 36% DNA sequence identify with. E. faecium sequences (JGI), and approximately one third of these sequences were completely absent in the draft genome. Non-ribosomal GFE sequences also encoded for 34 variable E. faecalis chromosomal regions, of which approximately 75% were independently determined in separate experiments (Table 7).

GFE was found to be a valid approach for identifying genetic differences between closely related microbial genomes.

Using this technique, the following were observed:
1. low average sequence identity for GFE sequences in the E. faecium genome;
2. the same variable chromosomal regions identified in two parallel experiments;
3. agreement of bioinformatic and experimental secondary screens for the specific strains studied; and
4. the absence of a high percentage of GFE clone sequences in the E. faecium draft genome (JGI).

While only a fraction of the clones from the enriched GFE libraries were sequenced, it is expected that additional cloning and sequencing would identify additional regions of genetic variation.

GFE Identified Regions of Variation within Highly Conserved DNA Sequences

The most highly conserved and relatively abundant sequences in the E. faecalis V583 genome are four ribosomal RNA (rrn) operons. Thirty one non-redundant clones were isolated, corresponding to ribosomal ISRs (n=3), 23S rRNA genes (n=22), and 16S rRNA genes (n=5). Ribosomal clones shared an average of 95.2% sequence identity with E. faecium homologous sequences, and were classified as false positives using the thresholds described above. However, short regions within 16S, 23S and ISR rrn sequences are also commonly used to differentiate between enterococci species (Patel et al., 1998; Monstein et al., 1998; Williams et al., 1001; Tsiodras et al., 2000; Gurtler et al., 1999; Hall, 1994; Naimi et al., 1997). For example, there are 59 polymorphic nucleotide positions (97.3% sequence identity) between two representative 16S rDNA sequences (Patel et al., 1998). There are only 14 such polymorphic nucleotides in a 300 bp stretch within domain V of the downstream 23S rDNA gene, and all 22 non-redundant 23S r DNA clones obtained by GFE fell within this variable domain V region.

ISR sequences are also widely recognized for their sequence variability and utility in both species identification and strain typing. Previous studies on *E. faecalis* report 16S-23S ISR sequence citations in the rrn operons, including the presence or absence of a tRNA$^{ala}$ gene, and a small number of intraspecies nucleotide substitutions (Gurtler et al., 1999; Hall, 1994; Neimi et al., 1997). Two GFE clones tested contained these previously described 16S-23S ISR sequences, one encoding for the tRNA$^{ala}$ gene, and one not. This indicates two distinct *E. faecalis* rrn operons in the ATCC #19433 strain. No tRNA-containing ISR sequences appeared in the *E. faecium* draft genome (JGI), as a BLASTn of this ISR sequence was unable to identify any similar sequences. These results demonstrate that GFE was able to obtain previously described species-specific short variable regions within highly conserved DNA sequences.

Identified *E. Faecalis* Genome Diversity Predominantly Represented in Surface Associated Sequences Genomic regions identified by GFE were predominantly genes predicted to encode for surface associated proteins. *E. faecium* V583 genome annotations indicating putative surface exposed or membrane associated proteins corresponded to 22.6% of the non-redundant GFE claims (Table 3). The overall frequency of genes annotated as encoding surface associated proteins in the genome is almost three times lower (6.4%). This over-representation suggests that one of the major differences between these species is the composition of proteins associated with the bacterial cell wall. Large sequence variation in genes involved in surface structures has also been observed in *Thermotoga maritime* (Nesbo et al., 2002) and also among several closely related pathogens (e.g., *Escherichia coli* 055 and 0157) genomes (Selander et al., 1997; Tarr et al., 2000; Tettelin et al., 2001; Tettelin et al., 2000). These observations are consistent with the idea that the genetic capacity for diverse surface proteins may be characteristic of the differences between closely related microorganisms. Several studies also suggest that this type of variation is due to diversifying selection pressure to avoid different host immune responses (Selander et al., 1997; Tettelin et al., 2000; Maiden et al., 1997). If this class of potential genetic markets does reflect proposed genetic variation, they would be of particular interest for the use of GFE in pathogenicity studies.

Host-Specific PCR Primers Targeting *Bacteriodales*-Like Sequences Exhibit a Wide Host Distribution Among Cattle In another study, GFE was used to enrich for DNA fragments isolated from an individual cow fecal metagenome that are absent in a single pig fecal metagenome. Dot blots confirmed the specificity of almost all GFE sequences for the cow fecal metagenome. In addition, three host-specific PCR primer sets were designed and optimized to target randomly selected GFE *Bacteriodales*-like DNA sequences (Table 8). All primer sets differentiated between the GFE target (cow) and blocker (pig) metagenomic DNA fragment pools, further demonstrating that GFE is a powerful approach for comparing two complex microbial communities. The ability of GFE to isolate DNA sequence between microbial communities was further demonstrated in similar experiments designed to select for microbial DNA sequences specific to human and chicken bacterial fecal communities.

Primers were then tested against 148 cow fecal samples to measure host distribution (Table 7). Host-specific PCR assays routinely amplified more than 80% of the cow fecal samples, regardless of geographic location. Host-specific PCR assays also showed remarkable stability within host animals over a 24-month time period. This surprising geographic and temporal stability, as well as widespread distribution among host populations, was unexpected, considering that GFE was limited to the comparison of two individual fecal samples.

Host-Specific PCR Primers Discriminate Among Many Animal Species

The unexpected stability and broad distribution of the PCR assays in cattle populations led to testing target specificity among other animal groups. All three host-specific primer sets showed extremely high levels of host specificity for cattle (Table 5), and are consistent with 16S rDNA phylogenetic studies reporting the presence of *Bacteroidales* host-specific endemic subpopulations in various animal fecal samples (Bernard and Field, 2000; Dick, 2005). Data also corroborates the notion that genes encoding for proteins directly involved in host-fecal microbe interactions will exhibit increased levels of specificity over 16S rRNA gene sequences (Simpson, 2002; Scott, 2004; Griffin, 1999; Jiang, 2001). Current 16S rDNA host-specific PCR assays can only discriminate between ruminant and non-ruminant fecal sources (Bernard and Field, 2000). Host-specific primers targeting non-ribosomal sequences differentiated between cattle and five other ruminant or pseudo-ruminant species including goat, sheep, alpaca, llama, and whitetail deer, with the exception of PCR assay 3, which cross-reacted with two alpaca fecal samples.

The present invention provides a widely applicable nucleic acid sorting method and its use in identifying regions of genetic variation between any two preparations of DNA such as two bacterial genomes or samples containing two microbial communities. GFE was able to identify *E. faecalis* DNA sequences that are absent in *E. faecium*, as well as cattle-, human-, and chicken-specific DNA sequences that are divergent or absent in other animal species fecal microbial communities. GFE provides a directed alternative to random genome sequencing for identifying genetic variation among bacterial genomes or microbial communities.

It is to be understood that the phraseology or terminology employed herein is for the purpose of description and not of limitation. The means and materials for carrying out various disclosed functions may take a variety of alternative forms without departing from the invention.

Thus, the expressions "means to . . ." and "means for . . ." as may be found in the specification above and/or in the claims below, followed by a functional statement, are intended to define and cover whatever structural, physical, chemical, or electrical element or structures which may now or in the future exist for carrying out the recited function, whether or not precisely equivalent to the embodiment or embodiments disclosed in the specification above. It is intended that such expressions be given their broadest interpretation.

REFERENCES

Althschul, S. F., Thomas, F., Madden, L., Scaffer, A., Zhang, J., Zhang, Z., Miller, W. and Lipman, D. (1997) *Nucleic Acids Research*, 25, 3389-3402.

Ausubel, F. M., Brent, R., Kingston, R. E., Moore, D. D., Seidman, J. G., Smith, J. A. and Struhl, K. (2001) *Current Protocols in Molecular Biology*, John Willey & Sons, New York.

Boucher, Y., Nesbø, C. L. and Doolittle, W. F. (2001) *Current Opinion in Microbiology*, 4, 285-289.

Dufour, A. P. (1984). U.S. Environmental Protection Agency, Cincinnati.

Galbraith, E. A., Antonopoulus, D. A. and White, B. A. (2004) *Environmental Microbiology*, 6, 928-937.

Graham, J. E. and Clark-Curtis, J. E. (1999) *Proceedings of the National Academy of Sciences of the United States of America*, 96, 11554-11559.

Grothues, D., Cantor, C. R. and Smith, C. L. (1993) *Nucleic Acids Research*, 21, 1321-1322.

Gürtler, V., YuJun, R. Pearson, S. R., Bates, S. M. and Mayall, B. C. (1999) *Microbiology*, 145, 1785-1796.

Hall, L. (1994) *Microbiology*, 140, 197-204.

Harwood, V. J., Delahoya, N. C., Ulrich, R. M., Kramer, M. F., Whitlock, J. E., Garey, J. R. and Lim, D. V. (2004) *Letters in Applied Microbiology*, 38, 476-482.

Kent, W. J. (2002) *Genome Research*, 12, 656-664.

Maiden, M. C. J., Suker, J. and Faevers, I. M. (1997) In van der Zeijst, B. A. M., Hoekstra, W. P. M., and van Embden, J. D. A. (ed.), *Ecology of pathogenic bacteria: molecular and evolutionary aspects*. Royal Netherlands Academy of Arts and Sciences, Amsterdam, pp. 15-43.

McLeod, M. P., Qin, X., Karpathy, S. E., Gioia, J., Highlander, S. K., Fox, G. E., McNeill, T. Z., Jiang, H., Muzny, D., Jacob, L. S. et al. (2004) *Science*, 186, 5842-5855.

Monstein, H. J., Quednau, H. J., Samuelsson, A., Ahrné, S., Isaksson, B. and Jonasson, J. (1998) *Microbiology*, 144, 1171-1179.

Naimi, A., Beck, G. and Branlant, C. (1997) *Microbiology*, 143, 823-834.

Nesbø, C. L., Nelson, K. E. and Doolittle, W. F. (2002) *Journal of Bacteriology*, 184, 4475-4488.

Patel, R. Piper, K. E., Rouse, M. S., Steckelberg, J. M., Uhl, J. R., Kohner, P., Hopkins, M. K., Cockerill, F. R., III and Kline, B. C. (1998) *Journal of Clinical Microbiology*, 36, 3399-3407.

Paulsen, I. T., Banerjei, L., Myers, G. S., Nelson, K. E., Seshadri, R., Read, T. D., Fouts, D. E., Eisen, J. A., Gill, S. R., Heidelberg, J. F., et al. (2003) *Science*, 299, 2071-2074.

Schaberg, D. R., Culver, D. H. and Gaynes, R. P. (1991) *American Journal of Medicine*, 91, 72S-75S.

Selander, R. K. (1997) In van der Zeijst, B. A., Hoekstra, W. P. M., and van Embden, J. D. A. (ed.), *Ecology of pathogenic bacteria: molecular and evolutionary aspects*. Royal Netherlands Academy of Arts and Sciences, Amsterdam, pp. 191-213.

Tarr, P. I., Schoening, L. M., Yea, Y. L., Ward, T. R., Jelacic, S, and Whittman, T. S. (2000) *Journal of Bacteriology*, 182, 6183-6191.

Tettelin, H., Nelson, K. E., Paulsen, I. T., Eisen, J. A., Read, T. D., Peterson, S. Heidelberg, J., DeBoy, R. T., Haft, D. H., Dodson, R. J. et al. (2001) *Science*, 293, 498-506.

Tettelin, H., Saunders, N. J., Heilderberg, J., Jeffries, A. C., Nelson, K. E., Eisen, J. A., Ketchum, K. A., Hood, D. W., Peden, J. F., Dodson, R. J. et al. (2000) *Sciences*, 287, 1809-1815.

Tsiodras, S., Golds, H. S., Coakely, E. P. G., Wennersten, C., Jr., M. and R. C. E., G. M. (2000) *Journal of Clinical Microbiology*, 38, 3991-3993.

Wilbur, W. J. and Lipman, D. J. (1983) *Proceedings of the National Academy of Sciences of the United States of America*, 80, 726-730.

Williams, A. M., Rodrigues, U. M. and Collins, M. D. (1991) *Research in Microbiology*, 145, 64-67.

---

What is claimed is:

1. A method for identifying differences between communities of microorganisms comprising:
   a) obtaining genomic DNA extracts from a first group of individual animal fecal samples and mixing these samples to create a first fecal microbial community DNA composite designated tester;
   b) obtaining genomic DNA fragments from a second group of animal fecal samples and using these samples to create a second fecal microbial community DNA composite designated blocker;
   c) labeling the tester and incubating the tester with the blocker
   d) obtaining labeled first genomic DNA fragments from a first community and hybridizing the first genomic DNA fragments with second genomic DNA fragments from a second community;
   e) incubating the first and second genomic fragments with additional genomic fragments from the first community containing defined terminal sequence tags to form DNA hybrids;
   f) capturing the resulting DNA hybrids formed with tags and PCR amplification of only the tagged fragments;
   g) obtaining enriched amounts of sequences unique to the first community; and h) identifying the enriched sequences thereby identifying the differences between the communities of microorganisms.

2. The method according to claim 1 wherein the tagged fragments are modified to work in real-time PCR assays.

3. The method according to claim 1 wherein the DNA is isolated from two bacterial microorganisms.

4. The method according to claim 3 wherein the first microorganism is *E. faecalis* and the second microorganism is *E. faecium*.

5. The method according to claim 1 wherein the first genomic DNA is labeled with biotin.

6. The method according to claim 1 wherein the first community is associated with chickens.

7. The method according to claim 1 wherein the first community is associated with pigs.

8. The method according to claim 1 wherein the first community is associated with humans.

9. A method for identifying genetic differences between two microbial genomes comprising:
   a) obtaining labeled first genomic DNA fragments from a first microorganism and hybridizing the first genomic DNA fragments with second genomic DNA fragments from a second microorganism;
   b) incubating the first and second genomic fragments with additional genomic fragments from the first microorganism containing defined terminal sequence tags;
   c) capturing the resulting DNA hybrids formed with tags and PCR amplification of only the tagged fragments;
   d) obtaining enriched amounts of sequences unique to the first microorganism; and
   e) identifying the enriched sequences thereby identifying the differences between two microbial genomes.

10. The method according to claim 9 wherein the tagged fragments are modified to work in real-time PCR.

* * * * *

SEQUENCE LISTING

```
<160> NUMBER OF SEQ ID NOS: 64

<210> SEQ ID NO 1
<211> LENGTH: 20
<212> TYPE: DNA
<213> ORGANISM: Artificial
<220> FEATURE:
<223> OTHER INFORMATION: Synthetic

<400> SEQUENCE: 1
tgcaatgtat cagcctcttc                                                  20

<210> SEQ ID NO 2
<211> LENGTH: 18
<212> TYPE: DNA
<213> ORGANISM: Artificial
<220> FEATURE:
<223> OTHER INFORMATION: Synthetic

<400> SEQUENCE: 2
agggcaaact cacgacag                                                    18

<210> SEQ ID NO 3
<211> LENGTH: 23
<212> TYPE: DNA
<213> ORGANISM: Artificial
<220> FEATURE:
<223> OTHER INFORMATION: Synthetic

<400> SEQUENCE: 3
acaagccagg tgatacagaa aga                                              23

<210> SEQ ID NO 4
```

```
<211> LENGTH: 24
<212> TYPE: DNA
<213> ORGANISM: Artificial
<220> FEATURE:
<223> OTHER INFORMATION: Synthetic

<400> SEQUENCE: 4
gcttgttgcg ttccttgaga taat                                          24

<210> SEQ ID NO 5
<211> LENGTH: 23
<212> TYPE: DNA
<213> ORGANISM: Artificial
<220> FEATURE:
<223> OTHER INFORMATION: Synthetic

<400> SEQUENCE: 5
ctaatggaaa atggatggta tct                                           23

<210> SEQ ID NO 6
<211> LENGTH: 18
<212> TYPE: DNA
<213> ORGANISM: Artificial
<220> FEATURE:
<223> OTHER INFORMATION: Synthetic

<400> SEQUENCE: 6
gccgcccagc tcaaatag                                                 18

<210> SEQ ID NO 7
<211> LENGTH: 20
<212> TYPE: DNA
<213> ORGANISM: Artificial
<220> FEATURE:
<223> OTHER INFORMATION: Synthetic

<400> SEQUENCE: 7
tgggaatggc ggtaatctcg                                               20

<210> SEQ ID NO 8
<211> LENGTH: 20
<212> TYPE: DNA
<213> ORGANISM: Artificial
<220> FEATURE:
<223> OTHER INFORMATION: Synthetic

<400> SEQUENCE: 8
caacagccgg tcgtcttcct                                               20

<210> SEQ ID NO 9
<211> LENGTH: 21
<212> TYPE: DNA
<213> ORGANISM: Artificial
<220> FEATURE:
<223> OTHER INFORMATION: Synthetic

<400> SEQUENCE: 9
actccctgcg ctccgaagat a                                             21

<210> SEQ ID NO 10
<211> LENGTH: 21
<212> TYPE: DNA
<213> ORGANISM: Artificial
<220> FEATURE:
<223> OTHER INFORMATION: Synthetic

<400> SEQUENCE: 10
```

```
ggcccaggca ccatttacag t                                          21
```

<210> SEQ ID NO 11
<211> LENGTH: 24
<212> TYPE: DNA
<213> ORGANISM: Artificial
<220> FEATURE:
<223> OTHER INFORMATION: Synthetic

<400> SEQUENCE: 11

```
ctccgtcttt ctccgtcctg ttct                                       24
```

<210> SEQ ID NO 12
<211> LENGTH: 21
<212> TYPE: DNA
<213> ORGANISM: Artificial
<220> FEATURE:
<223> OTHER INFORMATION: Synthetic

<400> SEQUENCE: 12

```
gatcccctc gcctccgtcc t                                           21
```

<210> SEQ ID NO 13
<211> LENGTH: 21
<212> TYPE: DNA
<213> ORGANISM: Artificial
<220> FEATURE:
<223> OTHER INFORMATION: Synthetic

<400> SEQUENCE: 13

```
taaaggtccc ggagaaggta t                                          21
```

<210> SEQ ID NO 14
<211> LENGTH: 20
<212> TYPE: DNA
<213> ORGANISM: Artificial
<220> FEATURE:
<223> OTHER INFORMATION: Synthetic

<400> SEQUENCE: 14

```
aatccggatg cgttttaga                                             20
```

<210> SEQ ID NO 15
<211> LENGTH: 22
<212> TYPE: DNA
<213> ORGANISM: Artificial
<220> FEATURE:
<223> OTHER INFORMATION: Synthetic

<400> SEQUENCE: 15

```
cgtcaggttt gtttcggtat tg                                         22
```

<210> SEQ ID NO 16
<211> LENGTH: 24
<212> TYPE: DNA
<213> ORGANISM: Artificial
<220> FEATURE:
<223> OTHER INFORMATION: Synthetic

<400> SEQUENCE: 16

```
aaggtgaagg tctggctgat gtaa                                       24
```

<210> SEQ ID NO 17
<211> LENGTH: 23
<212> TYPE: DNA
<213> ORGANISM: Artificial
<220> FEATURE:

<223> OTHER INFORMATION: Synthetic

<400> SEQUENCE: 17
gtaattcgcg ttcttcctca cat    23

<210> SEQ ID NO 18
<211> LENGTH: 23
<212> TYPE: DNA
<213> ORGANISM: Artificial
<220> FEATURE:
<223> OTHER INFORMATION: Synthetic

<400> SEQUENCE: 18
acctgcaaac cgtacaagaa aaa    23

<210> SEQ ID NO 19
<211> LENGTH: 20
<212> TYPE: DNA
<213> ORGANISM: Artificial
<220> FEATURE:
<223> OTHER INFORMATION: Synthetic

<400> SEQUENCE: 19
ccaacggcgt aacttcttca    20

<210> SEQ ID NO 20
<211> LENGTH: 23
<212> TYPE: DNA
<213> ORGANISM: Artificial
<220> FEATURE:
<223> OTHER INFORMATION: Synthetic

<400> SEQUENCE: 20
attaccggat tacaaacctt atg    23

<210> SEQ ID NO 21
<211> LENGTH: 20
<212> TYPE: DNA
<213> ORGANISM: Artificial
<220> FEATURE:
<223> OTHER INFORMATION: Synthetic

<400> SEQUENCE: 21
tatttctggg tgcggttgta    20

<210> SEQ ID NO 22
<211> LENGTH: 19
<212> TYPE: DNA
<213> ORGANISM: Artificial
<220> FEATURE:
<223> OTHER INFORMATION: Synthetic

<400> SEQUENCE: 22
ctgaccggaa tgactccca    19

<210> SEQ ID NO 23
<211> LENGTH: 21
<212> TYPE: DNA
<213> ORGANISM: Artificial
<220> FEATURE:
<223> OTHER INFORMATION: Synthetic

<400> SEQUENCE: 23
ctggagatca tcgttgacag a    21

<210> SEQ ID NO 24

```
<211> LENGTH: 20
<212> TYPE: DNA
<213> ORGANISM: Artificial
<220> FEATURE:
<223> OTHER INFORMATION: Synthetic

<400> SEQUENCE: 24
taggctcaag cagtaccgga                                             20

<210> SEQ ID NO 25
<211> LENGTH: 18
<212> TYPE: DNA
<213> ORGANISM: Artificial
<220> FEATURE:
<223> OTHER INFORMATION: Synthetic

<400> SEQUENCE: 25
cgtgaatttc cgctacga                                               18

<210> SEQ ID NO 26
<211> LENGTH: 18
<212> TYPE: DNA
<213> ORGANISM: Artificial
<220> FEATURE:
<223> OTHER INFORMATION: Synthetic

<400> SEQUENCE: 26
cctcttcctt gcgtccca                                               18

<210> SEQ ID NO 27
<211> LENGTH: 21
<212> TYPE: DNA
<213> ORGANISM: Artificial
<220> FEATURE:
<223> OTHER INFORMATION: Synthetic

<400> SEQUENCE: 27
cggccaaata ctcctgatcg t                                           21

<210> SEQ ID NO 28
<211> LENGTH: 24
<212> TYPE: DNA
<213> ORGANISM: Artificial
<220> FEATURE:
<223> OTHER INFORMATION: Synthetic

<400> SEQUENCE: 28
gcttgttgcg ttccttgaga taat                                        24

<210> SEQ ID NO 29
<211> LENGTH: 26
<212> TYPE: DNA
<213> ORGANISM: Artificial
<220> FEATURE:
<223> OTHER INFORMATION: Synthetic

<400> SEQUENCE: 29
cctctaatgg aaaatggatg gtatct                                      26

<210> SEQ ID NO 30
<211> LENGTH: 24
<212> TYPE: DNA
<213> ORGANISM: Artificial
<220> FEATURE:
<223> OTHER INFORMATION: Synthetic

<400> SEQUENCE: 30
```

```
ccatacttcg cctgctaata cctt                                              24
```

<210> SEQ ID NO 31
<211> LENGTH: 36
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Nucleotide 1 is modified by [DFAM].
<220> FEATURE:
<221> NAME/KEY: misc_feature
<222> LOCATION: (36)..(36)
<223> OTHER INFORMATION: Nucleotide 36 is modified by [DTAM].

<400> SEQUENCE: 31

```
aggcacctat gtcctttacc tcatcaacta cagaca                                 36
```

<210> SEQ ID NO 32
<211> LENGTH: 22
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Nucleotide 1 is modified by [DFAM].
<220> FEATURE:
<221> NAME/KEY: misc_feature
<222> LOCATION: (22)..(22)
<223> OTHER INFORMATION: Nucleotide 22 is modified by [DTAM].

<400> SEQUENCE: 32

```
ttatgcattg agcatcgagg cc                                                22
```

<210> SEQ ID NO 33
<211> LENGTH: 35
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (27)..(35)
<223> OTHER INFORMATION: n is a, c, g, or t

<400> SEQUENCE: 33

```
gacactctcg agacatcacc ggtaccnnnn nnnnn                                  35
```

<210> SEQ ID NO 34
<211> LENGTH: 22
<212> TYPE: DNA
<213> ORGANISM: Artificial
<220> FEATURE:
<223> OTHER INFORMATION: Synthetic

<400> SEQUENCE: 34

```
gacactctcg agacatcacc gg                                                22
```

<210> SEQ ID NO 35
<211> LENGTH: 23
<212> TYPE: DNA
<213> ORGANISM: Artificial
<220> FEATURE:
<223> OTHER INFORMATION: Synthetic

<400> SEQUENCE: 35

```
gacactctcc gagacatcac cgg                                            23

<210> SEQ ID NO 36
<211> LENGTH: 16
<212> TYPE: DNA
<213> ORGANISM: Artificial
<220> FEATURE:
<223> OTHER INFORMATION: Synthetic

<400> SEQUENCE: 36
gtaaaacgac ggccag                                                    16

<210> SEQ ID NO 37
<211> LENGTH: 17
<212> TYPE: DNA
<213> ORGANISM: Artificial
<220> FEATURE:
<223> OTHER INFORMATION: Synthetic

<400> SEQUENCE: 37
caggaaacag ctatgca                                                   17

<210> SEQ ID NO 38
<211> LENGTH: 29
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (21)..(29)
<223> OTHER INFORMATION: n is a, c, g, or t

<400> SEQUENCE: 38
gccggagctc tgcagaattc nnnnnnnnn                                      29

<210> SEQ ID NO 39
<211> LENGTH: 21
<212> TYPE: DNA
<213> ORGANISM: Artificial
<220> FEATURE:
<223> OTHER INFORMATION: Synthetic

<400> SEQUENCE: 39
gccggagctc tgcasgaatt c                                              21

<210> SEQ ID NO 40
<211> LENGTH: 40
<212> TYPE: DNA
<213> ORGANISM: Bacteriaroides fragilis

<400> SEQUENCE: 40
ccatccacag cacgtcgtaa gatcttcatc cagtacggca                          40

<210> SEQ ID NO 41
<211> LENGTH: 40
<212> TYPE: DNA
<213> ORGANISM: B. Thetaiotaomicron

<400> SEQUENCE: 41
cgaagcggag aagaacaaga gttccgcaac gtagaggaaa                          40

<210> SEQ ID NO 42
<211> LENGTH: 37
<212> TYPE: DNA
<213> ORGANISM: B. fragilis
```

```
<400> SEQUENCE: 42
ggcaagcctc aatcgcatgt tctggtcgtt gggctga                                37

<210> SEQ ID NO 43
<211> LENGTH: 36
<212> TYPE: DNA
<213> ORGANISM: Clostridium thermocellum

<400> SEQUENCE: 43
ctccaggatt tcgtgggaaa ggagcagctg acggca                                 36

<210> SEQ ID NO 44
<211> LENGTH: 42
<212> TYPE: DNA
<213> ORGANISM: Desulfitobacterium hafniense

<400> SEQUENCE: 44
gacgagatct atatttgcct cacggagcat atcctacgat ca                          42

<210> SEQ ID NO 45
<211> LENGTH: 36
<212> TYPE: DNA
<213> ORGANISM: B. fragilis

<400> SEQUENCE: 45
cgtgaatttc cgctacgacc tcttccttgc gtccca                                 36

<210> SEQ ID NO 46
<211> LENGTH: 42
<212> TYPE: DNA
<213> ORGANISM: C. tetani

<400> SEQUENCE: 46
ggcaggcatc aagtcaacat ggcaaaagca actgtcatgg ca                          42

<210> SEQ ID NO 47
<211> LENGTH: 39
<212> TYPE: DNA
<213> ORGANISM: B. fragilis

<400> SEQUENCE: 47
aggagcattt gtcgccctag gtaaagctgc ccggtaata                              39

<210> SEQ ID NO 48
<211> LENGTH: 38
<212> TYPE: DNA
<213> ORGANISM: B. fragilis

<400> SEQUENCE: 48
tacccgcaac ggggagaacc gatgatacgc tttcccaa                               38

<210> SEQ ID NO 49
<211> LENGTH: 41
<212> TYPE: DNA
<213> ORGANISM: C. perfringens str.

<400> SEQUENCE: 49
ctggagatca tcgttgacag ataggctcaa gcagtaccgg a                           41

<210> SEQ ID NO 50
<211> LENGTH: 40
<212> TYPE: DNA
<213> ORGANISM: B. thetaiotaomicron
```

```
<400> SEQUENCE: 50
cctgtcgtaa aacccggggt cttcgatttt ccctgtttca                         40

<210> SEQ ID NO 51
<211> LENGTH: 39
<212> TYPE: DNA
<213> ORGANISM: B. thetaiotaomicron

<400> SEQUENCE: 51
tatttctggg tgcggttgta ctgaccggaa tgactccca                          39

<210> SEQ ID NO 52
<211> LENGTH: 40
<212> TYPE: DNA
<213> ORGANISM: B. fragilis

<400> SEQUENCE: 52
gtgcgaccga tatggaccag agacatcacc ggaaacaaca                         40

<210> SEQ ID NO 53
<211> LENGTH: 40
<212> TYPE: DNA
<213> ORGANISM: B. fragilis

<400> SEQUENCE: 53
agacatcacc ggcaataact acaaggagct atgccgctta                         40

<210> SEQ ID NO 54
<211> LENGTH: 43
<212> TYPE: DNA
<213> ORGANISM: B. fragilis

<400> SEQUENCE: 54
gtaagacagc aaccccatgt aacctatggt tcaacacgct tta                     43

<210> SEQ ID NO 55
<211> LENGTH: 38
<212> TYPE: DNA
<213> ORGANISM: B. fragilis

<400> SEQUENCE: 55
ctttgctgca agctccttga tacggaagcg gaggaaag                           38

<210> SEQ ID NO 56
<211> LENGTH: 41
<212> TYPE: DNA
<213> ORGANISM: Lactobacillus acidophilus

<400> SEQUENCE: 56
gatctgggtc atttggattg agttgaaggc gcaactgtaa a                       41

<210> SEQ ID NO 57
<211> LENGTH: 38
<212> TYPE: DNA
<213> ORGANISM: Clostridiaceae

<400> SEQUENCE: 57
gacagtccta tggatgccca aaaacggcag cgcaaaga                           38

<210> SEQ ID NO 58
<211> LENGTH: 34
<212> TYPE: DNA
<213> ORGANISM: B. fragilis
```

-continued

```
<400> SEQUENCE: 58
cgcctgcgtt ccctttaaat gggcgcaagc ctga                                    34

<210> SEQ ID NO 59
<211> LENGTH: 38
<212> TYPE: DNA
<213> ORGANISM: B. fragilis

<400> SEQUENCE: 59
atcggctacg atttccgtta tgttcgtcgc atggctca                                38

<210> SEQ ID NO 60
<211> LENGTH: 40
<212> TYPE: DNA
<213> ORGANISM: Bifidobacterium sp.

<400> SEQUENCE: 60
gaacagggag gcgtcttgag cgtgcaggcc cagacccgta                              40

<210> SEQ ID NO 61
<211> LENGTH: 39
<212> TYPE: DNA
<213> ORGANISM: B. fragilis

<400> SEQUENCE: 61
ggaaatcaca gttttgggga cgcatggagg acgatggta                               39

<210> SEQ ID NO 62
<211> LENGTH: 37
<212> TYPE: DNA
<213> ORGANISM: C. thermocellum

<400> SEQUENCE: 62
ggctgcctgc tcgtctacaa gcggcctctt gagtcca                                 37

<210> SEQ ID NO 63
<211> LENGTH: 38
<212> TYPE: DNA
<213> ORGANISM: C. tetani

<400> SEQUENCE: 63
gtccagcgcc tcattgattg gtgatcgact tttccaat                                38

<210> SEQ ID NO 64
<211> LENGTH: 42
<212> TYPE: DNA
<213> ORGANISM: L. gasseri

<400> SEQUENCE: 64
accattttgc ttgtcactgc caaatgtaag ccgcaaagat ga                           42
```